(12) United States Patent
Ammann et al.

(10) Patent No.: US 10,875,866 B2
(45) Date of Patent: Dec. 29, 2020

(54) PYRROLO[1,2-B]PYRIDAZINE DERIVATIVES

(71) Applicant: Gilead Sciences, Inc., Foster City, CA (US)

(72) Inventors: Stephen Ammann, Redwood City, CA (US); Elizabeth M. Bacon, Burlingame, CA (US); Gediminas Brizgys, San Carlos, CA (US); Elbert Chin, San Mateo, CA (US); Chienhung Chou, Dublin, CA (US); Jeromy J. Cottell, Redwood City, CA (US); Marilyn Ndukwe, Menlo Park, CA (US); James G. Taylor, Burlingame, CA (US); Nathan E. Wright, Foster City, CA (US); Zheng-Yu Yang, Palo Alto, CA (US); Sheila M. Zipfel, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/508,979

(22) Filed: Jul. 11, 2019

(65) Prior Publication Data

US 2020/0017510 A1 Jan. 16, 2020

Related U.S. Application Data

(60) Provisional application No. 62/697,533, filed on Jul. 13, 2018.

(51) Int. Cl.
*A61K 31/519* (2006.01)
*C07D 487/04* (2006.01)

(52) U.S. Cl.
CPC ................. *C07D 487/04* (2013.01)

(58) Field of Classification Search
CPC ............... A61K 31/519; C07D 487/04
USPC .......................... 514/248; 544/238
See application file for complete search history.

(56) References Cited

U.S. PATENT DOCUMENTS

| | | | |
|---|---|---|---|
| 8,293,923 B2 | 10/2012 | Guckian et al. |
| 8,987,311 B2 | 3/2015 | Dodd et al. |
| 9,067,948 B2 | 6/2015 | Harriman et al. |
| 9,073,892 B2 | 7/2015 | Jorand-Lebrun et al. |
| 9,169,252 B2 | 10/2015 | Santella et al. |
| 9,169,260 B2 | 10/2015 | McElroy et al. |
| 9,212,190 B2 | 12/2015 | Harriman et al. |
| 9,216,991 B2 | 12/2015 | Crosignani et al. |
| 9,221,809 B2 | 12/2015 | Seganish et al. |
| 9,242,975 B2 | 1/2016 | Paidi et al. |
| 9,255,110 B2 | 2/2016 | Arora et al. |
| 9,340,554 B2 | 5/2016 | Romero et al. |
| 9,518,065 B2 | 12/2016 | Romero et al. |
| 9,540,333 B2 | 1/2017 | Santella et al. |
| 9,546,153 B2 | 1/2017 | Bhide et al. |
| 9,567,320 B2 | 2/2017 | Jorand-Lebrun et al. |
| 9,586,948 B2 | 3/2017 | Seganish et al. |
| 9,598,440 B2 | 3/2017 | Seganish et al. |
| 9,657,009 B2 | 5/2017 | Bhide et al. |
| 9,732,095 B2 | 8/2017 | Gummadi et al. |
| 9,751,892 B2 | 9/2017 | Greenwood et al. |
| 9,765,059 B2 | 9/2017 | Collins et al. |
| 9,790,221 B2 | 10/2017 | Jorand-Lebrun et al. |
| 9,790,234 B2 | 10/2017 | Romero et al. |
| 9,815,836 B2 | 11/2017 | Chen et al. |
| 9,862,715 B2 | 1/2018 | Paidi et al. |
| 9,879,022 B2 | 1/2018 | Trzupek et al. |
| 9,890,145 B2 | 2/2018 | Yoshida et al. |
| 9,890,152 B2 | 2/2018 | Bryan et al. |
| 9,926,330 B2 | 3/2018 | Altman et al. |
| 9,932,350 B2 | 4/2018 | Altman et al. |
| 9,943,516 B2 | 4/2018 | Altman et al. |
| 9,951,064 B2 | 4/2018 | Bryan et al. |
| 9,951,086 B2 | 4/2018 | Bothe et al. |
| 9,969,710 B2 | 5/2018 | Jorand-Lebrun et al. |
| 9,969,749 B2 | 5/2018 | Altman et al. |
| 9,982,000 B2 | 5/2018 | Kelley et al. |
| 10,000,480 B2 | 6/2018 | Moslin et al. |
| 10,030,034 B2 | 7/2018 | Ho et al. |
| 10,064,861 B2 | 9/2018 | Jorand-Lebrun et al. |
| 10,336,762 B2 | 7/2019 | Bacon et al. |
| 2003/0144286 A1 | 7/2003 | Frenkel et al. |
| 2007/0037803 A1 | 2/2007 | Frenkel et al. |
| 2012/0015962 A1 | 1/2012 | Arora et al. |
| 2012/0115861 A1 | 5/2012 | Calderini et al. |
| 2012/0283238 A1 | 11/2012 | Romero et al. |
| 2013/0274241 A1 | 10/2013 | Jorand-Lebrun et al. |

(Continued)

FOREIGN PATENT DOCUMENTS

JP 2012-254939 A 12/2012
WO WO-2008/016643 A2 2/2008
(Continued)

OTHER PUBLICATIONS

Balasubramanian, W.R. et al. (2016) "Efficacy and safety of highly selective novel IRAK4 inhibitors for treatment of ABC-DLBCL" Abstract #4798, Aurigene Discovery Technologies, Bangalore, India.
(Continued)

*Primary Examiner* — Jeffrey H Murray

(57) ABSTRACT

A compound of Formula (I):

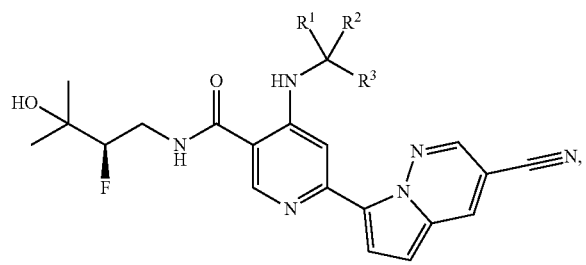

pharmaceutically acceptable salts thereof, deuterated analogs thereof, compositions thereof, and methods of treating disease using a compound thereof, wherein the variable substituents are disclosed herein.

6 Claims, No Drawings

(56) References Cited

U.S. PATENT DOCUMENTS

| | | |
|---|---|---|
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0155379 A1 | 6/2014 | Ho et al. |
| 2014/0194417 A1 | 7/2014 | Greenwood et al. |
| 2014/0315925 A1 | 10/2014 | Collins et al. |
| 2015/0018344 A1 | 1/2015 | Paidi et al. |
| 2015/0045347 A1 | 2/2015 | Dodd et al. |
| 2015/0133451 A1 | 5/2015 | Yoshida et al. |
| 2015/0284405 A1 | 10/2015 | Trzupek et al. |
| 2015/0299183 A1 | 10/2015 | Moslin et al. |
| 2015/0329498 A1 | 11/2015 | Romero et al. |
| 2015/0376206 A1 | 12/2015 | Jorand-Lebrun et al. |
| 2016/0002265 A1 | 1/2016 | Jenkins et al. |
| 2016/0166576 A1 | 6/2016 | Lim et al. |
| 2016/0207936 A1 | 7/2016 | Arora et al. |
| 2016/0229856 A1 | 8/2016 | Chen et al. |
| 2016/0229871 A1 | 8/2016 | Chen et al. |
| 2016/0326151 A1 | 11/2016 | Gummadi et al. |
| 2017/0037041 A1 | 2/2017 | Yen et al. |
| 2017/0081317 A1 | 3/2017 | Jorand-Lebrun et al. |
| 2017/0152263 A1 | 6/2017 | Gummadi et al. |
| 2017/0204093 A1 | 7/2017 | Chan et al. |
| 2017/0349570 A1 | 12/2017 | Bothe et al. |
| 2017/0369476 A1 | 12/2017 | Chen et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0111917 A1 | 4/2018 | Tso et al. |
| 2018/0169094 A1 | 6/2018 | Jorand-Lebrun et al. |
| 2018/0179213 A1 | 6/2018 | Duncia et al. |
| 2018/0186799 A1 | 7/2018 | Gardner et al. |
| 2018/0201609 A1 | 7/2018 | Gummadi et al. |
| 2018/0208605 A1 | 7/2018 | Gummadi et al. |
| 2018/0214447 A1 | 8/2018 | Ben Neriah et al. |
| 2018/0230127 A1 | 8/2018 | Anderson et al. |
| 2018/0237426 A1 | 8/2018 | Jorand-Lebrun et al. |
| 2018/0244646 A1 | 8/2018 | Lee et al. |
| 2018/0244677 A1 | 8/2018 | Xu et al. |
| 2018/0289685 A1 | 10/2018 | Bothe et al. |
| 2018/0298015 A1 | 10/2018 | Bryan et al. |
| 2018/0305351 A1 | 10/2018 | Brys et al. |
| 2019/0106407 A1 | 4/2019 | Thaler et al. |
| 2019/0292191 A1 | 9/2019 | Duncia et al. |

FOREIGN PATENT DOCUMENTS

| | | | |
|---|---|---|---|
| WO | WO-2011/043371 A1 | 4/2011 | |
| WO | WO-2013/042137 A1 | 3/2013 | |
| WO | WO-2017/004133 A1 | 1/2017 | |
| WO | WO-2017/004134 A1 | 1/2017 | |
| WO | WO-2017/024589 A1 | 2/2017 | |
| WO | WO-2017/108744 A1 | 6/2017 | |
| WO | WO-2017/127430 A1 | 7/2017 | |
| WO | WO-2017/205762 A1 | 11/2017 | |
| WO | WO-2017/205766 A1 | 11/2017 | |
| WO | WO-2017/205769 A1 | 11/2017 | |
| WO | WO-2017/207385 A1 | 12/2017 | |
| WO | WO-2018/083085 A1 | 5/2018 | |

OTHER PUBLICATIONS

Bhide, R.S. et al. (2017) "Discovery and structure-based design of 4,6-diaminonicotinamides as potent and selective IRAK4 inhibitors" *Bioorg Med Chem Lett.* 27(21):4908-4913.

Buckley, G.M. et al. (2008) "IRAK-4 inhibitors. Part 1: A series of amides" *Bioorg Med Chem Lett.* 18:3211-3214.

Buckley, G.M. et al. (2008) "IRAK-4 inhibitors. Part II: A structure-based assessment of imidazo[1,2-a]pyridine binding" *Bioorg Med Chem Lett.* 18:3291-3295.

Buckley, G.M. et al. (2008) "IRAK-4 inhibitors. Part III: A series of imidazo[1,2-a]pyridines" *Bioorg Med Chem Lett.* 18:3656-3660.

Chaudhary, D. et al. (2012) "Identification of Highly Potent and Selective Interleukin-1 Receptor-Associated Kinase 4 Inhibitors for the Treatment of Rheumatic Diseases" Poster, Nimbus Discovery.

Chaudhary, D. et al. (2015) "Recent advances in the discovery of small molecule inhibitors of interleukin-1 receptor-associated kinase 4 (IRAK4) as a therapeutic target for inflammation and oncology disorders" *J Med Chem.* 58(1):96-110.

Cushing, L. et al. (2014) "Interleukin 1/Toll-like Receptor-induced Autophosphorylation Activates Interleukin 1 Receptor-associated Kinase 4 and Controls Cytokine Induction in a Cell Type-specific Manner" *Journal of Biological Chemistry* 289(15):10865-10875.

Danker, T. et al. (2014) "Early identification of hERG liability in drug discovery programs by automated patch clamp" *Frontiers in Pharmacology* 5(203):1-11.

Dudhgaonkar, S. et al. (2017) "Selective IRAK4 Inhibition Attenuates Disease in Murine Lupus Models and Demonstrates Steroid Sparing Activity" *J Immunol.* 198(3):1308-1319.

Hynes, J. et al. (2016) "Discovery of pyridine amide based inhibitors of interleukin receptor-associated kinase 4 (IRAK4) for the treatment of lupus" Abstract #201, ASC, MEDI: Division of Medicinal Chemistry.

Kelly, P.N. et al. (2015) "Selective interleukin-1 receptor-associated kinase 4 inhibitors for the treatment of autoimmune disorders and lymphoid malignancy" *J Exp Med.* 212(13):2189-2201.

Lainchbury, M. et al. (2012) "Discovery of 3-Alkoxyamino-5-(pyridin-2-ylamino)pyrazine-2-carbonitriles as Selective, Orally Bioavailable CHK1 Inhibitors" *J Med Chem.* 55:10229-10240.

Lim, J. et al. (2015) "Discovery of 5-Amino-N-(1H-pyrazol-4-yl)pyrazolo[1,5-a]pyrimidine-3-carboxamide Inhibitors of IRAK4" *ACS Med Chem Lett.* 6(6):683-688.

McElroy, W.T. et al. (2015) "Discovery and hit-to-lead optimization of 2,6-diaminopyrimidine inhibitors of interleukin-1 receptor-associated kinase 4" *Bioorg Med Chem Lett.* 25:1836-1841.

McElroy, W.T. et al. (2015) "Potent and Selective Amidopyrazole Inhibitors of IRAK4 That Are Efficacious in a Rodent Model of Inflammation" *ACS Med Chem Lett.* 6:677-682.

Nolan, R.P. et al. (2013) "A mechanistic pharmacodynamic model of IRAK-4 drug inhibition in the Toll-like receptor pathway" *J Pharmacokinet Pharmacodyn* 40:609-622.

Picard, C. et al. (2011) "Infectious Diseases in Patients with IRAK-4, MyD88, NEMO, or IkBa Deficiency" *Clinical Microbiology Reviews* 24(3):490-497.

Powers, J.P. et al. (2006) "Discovery and initial SAR of inhibitors of interleukin-1 receptor-associated kinase-4" Bioorg Med Chem Lett. 16:2842-2845.

Seganish, W.M. (2016) "Inhibitors of interleukin-1 receptor-associated kinase 4 (IRAK4): a patent review (2012-2015)" *Expert Opinion on Therapeutic Patents* 26(8):917-932.

Seganish, W.M. et al. (2015) "Discovery and Structure Enabled Synthesis of 2,6-Diaminopyrimidin-4-one IRAK4 Inhibitors" *ACS Med Chem Lett.* 6:942-947.

Tumey, L.N. et al. (2014) "Identification and optimization of indolo[2,3-c]quinoline inhibitors of IRAK4" *Bioorg Med Chem Lett.* 24(9):2066-2072.

Vajda, E.G. et al. (2011) "Novel Small Molecule Inhibitors of Interleukin-1 Receptor Associated Kinase-4 Are Effective in a Preclinical Model of Arthritis" Presentation, Ligand Pharmaceuticals, Inc.

Wang, Z. et al. (2015) "Discovery of potent, selective, and orally bioavailable inhibitors of interleukin-1 receptor-associate kinase-4" *Bioorg Med Chem Lett.* 25:5546-5550.

Ligand (2014) "Interleukin-1 Receptor Associated Kinase-4 (IRAK4) Inhibitor Program" Summary, Presentation.

Intl. Search Report—Written Opinion dated Sep. 6, 2019 for PCT/US2019/041382.

Office Action dated Apr. 28, 2020 for Taiwanese Appl. No. 108123710.

Office Action dated May 26, 2020 for GCC Appl. No. 37899.

PYRROLO[1,2-B]PYRIDAZINE DERIVATIVES

CROSS-REFERENCE TO RELATED APPLICATIONS

This application claims priority under 35 U.S.C. § 119(e) to U.S. Provisional Application No. 62/697,533, filed Jul. 13, 2018, the content of which is incorporated by reference in its entirety.

FIELD

The present disclosure relates to novel compounds that are inhibitors of the kinase IRAK4. The disclosure also relates to methods for preparing the compounds and to pharmaceutical compositions comprising such compounds.

BACKGROUND

Interleukin-1 receptor-associated kinase-4 (IRAK4) is a serine-threonine kinase which acts as a mediator in interleukin-1/Toll-like receptor (IL-1/TLR) signaling cascades. More particularly, IRAK4 is involved in activation of adaptor protein myeloid differentiation primary response gene 88 (MyD88) signaling cascades and is hypothesized to play a role in inflammatory and fibrotic disorders, such as rheumatoid arthritis (RA), inflammatory bowel disease (IBD), gout, Lyme disease, arthritis, psoriasis, pelvic inflammatory disease, systemic lupus erythematosus (SLE), Sjogren's syndrome, viral myocarditis, acute and chronic tissue injury, non-alcoholic steatohepatitis (NASH), alcoholic hepatitis and kidney disease, including chronic kidney disease and diabetic kidney disease. In addition, IRAK4 plays a role in certain cancers and is hypothesized to play a role in inflammation associated with gastrointestinal infections, including *C. difficile*. Signaling through IL-1R/TLR results in the activation of MyD88 which recruits IRAK4 and IRAK1 to form a signaling complex. This complex then interacts with a series of kinases, adaptor proteins, and ligases, ultimately resulting in the activation of nuclear factor kappa-light-chain-enhancer of activated B cells (NF-κB), activator protein-1 (API), cyclic AMP-responsive element-binding protein (CREB) and the interferon-regulatory factors (IRFs), including IRF5 and IRF7, inducing the generation of proinflammatory cytokines and type I interferons.

Therefore, inhibitors of IRAK4 may be useful in the treatment of inflammatory and fibrotic disorders, such as rheumatoid arthritis (RA), inflammatory bowel disease (IBD), gout, Lyme disease, arthritis, psoriasis, pelvic inflammatory disease, systemic lupus erythematosus (SLE), Sjogren's syndrome, inflammation associated with gastrointestinal infections, including *C. difficile*, viral myocarditis, acute and chronic tissue injury, non-alcoholic steatohepatitis (NASH), alcoholic hepatitis and kidney disease, including chronic kidney disease and diabetic kidney disease. (Joosten, L. A. B et al., TOLL-LIKE RECEPTORS AND CHRONIC INFLAMMATION IN RHEUMATIC DISEASES: NEW DEVELOPMENTS, Nat. Rev. Rheumatol., 346|June 2016, 12; 344-357 Published online 12 May 2016) (Valaperti, A. et al., INNATE IMMUNE INTERLEUKIN-1RECEPTOR-ASSOCIATED KINASE 4 EXACERBATES VIRAL MYOCARDITIS BY REDUCING CCR5$^+$CD11b$^+$ MONOCYTE MIGRATION AND IMPAIRING INTERFERON PRODUCTION, Circulation, 128 Sep. 2013 14; 1542-1554), as well as Type I interferonopathies, such as Aicardi-Goutières syndrome, Familial chilblain lupus, and Retinal vasculopathy with cerebral leukodystrophy, (Lee-Kirsch et al., TYPE I INTERFERONOPATHIES—AN EXPANDING DISEASE SPECTRUM OF IMMUNODYSREGULATION, Semin. Immunopathol. (2015) 37:349-357), (Leaf, I. A. et al., PERICYTE MYD88 AND IRAK4 CONTROL INFLAMMATORY AND FIBROTIC RESPONSES TO TISSUE INJURY, The Journal of Clinical Investigation, 127|January 2017, 1; 321-334), (Seki, E. et al., TLR4 ENHANCES TGF-β SIGNALING AND HEPATIC FIBROSIS, Nature Medicine, 13|Nov. 2007, 11; 1324-1332), (Garcia-Martinez, I. et al., HEPATOCYTE MITOCHONDRIAL DNA DRIVES NONALCHOLIC STEATOHEPATITIS BY ACTIVATION OF TLR9, The Journal of Clinical Investigation, 126|March 2016, 3; 859-864).

In addition, certain cancers, including lymphomas, may contain one or more mutations in the MYD88 adaptor protein, leading to a constitutively active signaling cascade that may promote survival of tumor cells. (Kelly et al., IRAK4 inhibitors for autoimmunity and lymphoma, J. Exp. Med. 2015 Vol. 212 No. 13 2189-2201)

Therefore, an inhibitor of IRAK4 may be useful in the treatment of cancers, including lymphomas.

There are currently no approved IRAK4 inhibiting pharmaceuticals. Therefore, it would be useful to provide an IRAK4 inhibiting compound with properties suitable for administration as a pharmaceutical agent to a mammal, particularly a human. Considerations for selecting a pharmaceutical compound are multifactorial. Compound characteristics including on-target potency, pharmacokinetics, pKa, solubility, stability (e.g., metabolic stability) and off-target liabilities (including potential cardiac toxicity), as well as potential drug-drug interactions are frequently profiled.

Inhibition of the cardiac ion channel coded by human ether-à-gogo-related gene (hERG) can lead to cardiac arrhythmia, which is a major concern in drug discovery and development. Automated electrophysiological patch clamp allows assessment of hERG channel effects early in drug development to aid medicinal chemistry programs and has become routine in pharmaceutical companies. *Early identification of hERG liability in drug discovery programs by automated patch clamp*, Front Pharmaco. (2 Sep. 2014); 5: 203.

WO2016210034, WO2016210036, WO2015150995, WO2016127024, and WO2016210037 recite compounds said to be useful as IRAK4 inhibitors.

SUMMARY OF THE INVENTION

Provided herein are compounds and pharmaceutical compositions useful as inhibitors of IRAK4. Some compounds of the disclosure may find use in pharmaceutical compositions, together with at least one pharmaceutically acceptable excipient, for treating a subject in need thereof. Compounds of the present disclosure also have been found to inhibit production of pro-inflammatory cytokines TNFα, IL-6, IL-1β, IL-8, IL-12, IL-23 and type I interferons IFNα and IFNβ, all of which are mediators of inflammation and the immune response. The disclosure also provides compositions, including pharmaceutical compositions, kits that include the compounds, and methods of using and making the compounds.

In one embodiment of the disclosure, there is provided a compound of Formula (I):

(I)

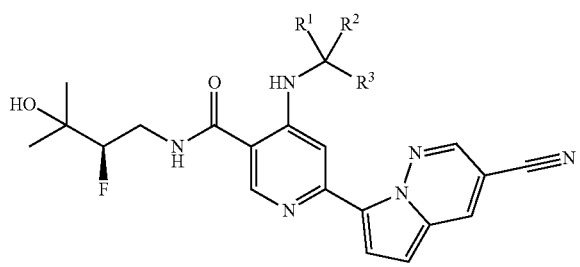

or a pharmaceutically acceptable salt or structural isomer thereof, wherein:

$R^1$ is selected from H, deuterium or $C_{1-4}$alkyl, and said $C_{1-4}$alkyl is optionally substituted with one or more halo;

$R^2$ is selected from H, deuterium or $C_{1-4}$alky, and said alkyl is optionally substituted with one or more halo; or $R^1$ and $R^2$, together with the carbon atoms to which they are attached, form a C3-C6 cycloalkyl; and $R^3$ is $C_{0-4}$alkyl-CN.

In an embodiment, $R^2$ is H.

In an embodiment, $R^1$ is methyl.

In an embodiment, $R^3$ is —CN.

In another embodiment there is provided a compound of Formula II:

(II)

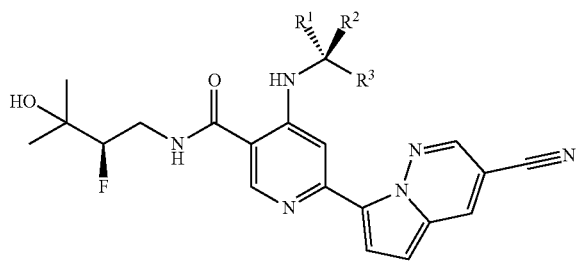

or a pharmaceutically acceptable salt or structural isomer thereof, wherein:

$R^1$ is selected from H, deuterium or $C_{1-4}$ alkyl, and said $C_{1-4}$alkyl has one or more hydrogen atoms optionally replaced with deuterium.

$R^2$ is selected from H, deuterium or $C_{1-4}$ alkyl, and said $C_{1-4}$alkyl has one or more hydrogen atoms optionally replaced with deuterium; and $R^3$ is $C_{0-4}$alkyl-CN.

In an embodiment of Formula (II), $R^2$ is H.

In another embodiment, $R^2$ is deuterium.

In an embodiment of Formula (II), $R^1$ is methyl.

In an embodiment of Formula (II), $R^1$ is methyl, with one or more hydrogen atoms attached to the methyl replaced with deuterium.

In an embodiment, $R^3$ is —CN.

In another embodiment, there is provided a compound of Formula (III):

(III)

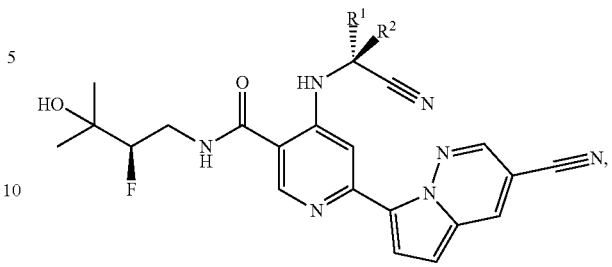

or a pharmaceutically acceptable salt, or deuterated analog thereof, wherein:

$R^1$ is H, deuterium or methyl, said methyl having one or more hydrogen atoms optionally replaced with deuterium.

In an embodiment, there is provided a compound having the structure:

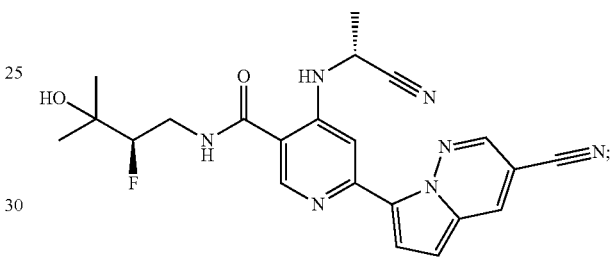

or a pharmaceutically acceptable salt thereof.

In an embodiment, there is provided a pharmaceutical composition comprising a compound herein, or a pharmaceutically acceptable salt thereof, together with a pharmaceutically acceptable carrier.

Another embodiment of the present disclosure provides a pharmaceutical composition comprising a compound of the disclosure, together with a pharmaceutically acceptable carrier, and optionally a diluent.

Another embodiment of the present disclosure provides a method of treating an inflammation related disease or disorder in a patient in need thereof, comprising administering to said patient a compound of the disclosure, or a pharmaceutical composition thereof.

DETAILED DESCRIPTION OF THE INVENTION

Definitions

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms. $C_0$ indicates that no carbons are present, or in other words, a bond to the next substituent.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Cyano" refers to the group —CN.

"Halo" refers to —F, —Cl, —Br, —I.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and as well as examples of aryl, such as phenyl or naphthyl and the like. Also, the term "any heterocyclyl" includes heterocyclyls, such as oxetanyl, tetrahydropyranyl, morpholino, piperidinyl and the like. In the same manner, the term "any heteroaryl" includes heteroaryls, such as pyridine, pyridazine, thiazole, thiadiazole, quinoline and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{15}O$, $^{18}O$, $^3F$, $^{32}F$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a nonisotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2(alkyl)$), dialkyl amines (i.e., $HN(alkyl)_2$), trialkyl amines (i.e., $N(alkyl)_3$), substituted alkyl amines (i.e., $NH_2(substituted\ alkyl)$), di(substituted alkyl) amines (i.e., $HN(substituted\ alkyl)_2$), tri(substituted alkyl) amines (i.e., $N(substituted\ alkyl)_3$), alkenyl amines (i.e., $NH_2(alkenyl)$), dialkenyl amines (i.e., $HN(alkenyl)_2$), trialkenyl amines (i.e., $N(alkenyl)_3$), substituted alkenyl amines (i.e., $NH_2(substituted\ alkenyl)$), di(substituted alkenyl) amines (i.e., $HN(substituted\ alkenyl)_2$), tri(substituted alkenyl) amines (i.e., $N(substituted\ alkenyl)_3$, mono-, di- or tri-cycloalkyl amines (i.e., $NH_2(cycloalkyl)$, $HN(cycloalkyl)_2$, $N(cycloalkyl)_3$), mono-, di- or tri-arylamines (i.e., $NH_2(aryl)$, $HN(aryl)_2$, $N(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted. One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Combinations

Patients being treated by administration of the IRAK4 inhibitors of the disclosure often exhibit diseases or conditions that benefit from treatment with other therapeutic agents. These diseases or conditions can be of an inflammatory nature or can be related to cancer, metabolic disorders, gastrointestinal disorders and the like. Thus, one aspect of the disclosure is a method of treating an inflammation related disease or condition, or a metabolic disorder, gastrointestinal disorder, or cancer and the like comprising administering a compound of the in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

Combinations for Inflammatory Diseases and Conditions

For example, a compound of the present disclosure may be combined with one or more 5-Lipoxygenase inhibitors, Acetylcholinesterase inhibitors, Acetyl-CoA carboxylase (ACC) inhibitors, ACTH receptor agonists, Activin receptor antagonists, Acyltransferase inhibitors, Adrenocorticotrophic hormone ligands, AKT1 gene inhibitors, Alkaline phosphatase modulators, Alkaline phosphatase stimulators, Androgen receptor agonists, Apolipoprotein C3 antagonists, ASK1 kinase inhibitors, Bactericidal permeability protein stimulators, Beta adrenoceptor antagonists, Beta-glucuronidase inhibitors, B-lymphocyte antigen CD20 inhibitors, Bradykinin receptor modulators, BTK kinase inhibitors, Calcineurin inhibitors, Calcium channel inhibitors, Cannabinoid CB1 receptor modulators, Cannabinoid CB2 receptor modulators, Cannabinoid receptor antagonists, Cannabinoid receptor modulators, Caspase inhibitors, Cathepsin S inhibitors, CCN protein stimulators, CCR3 chemokine antagonists, CCR5 chemokine antagonists, CCR9 chemokine antagonists, CD3 modulators, CD40 ligand inhibitors, CD40 ligand receptor antagonists, CD49b antagonists, CD49d antagonists, CD89 agonists, Cell adhesion molecule inhibitors, Chemokine CXC ligand inhibitors, CHST15 gene inhibitors, Collagen modulators, CSF-1 agonists, CSF-1 antagonists, CXC10 chemokine ligand inhibitors, CXCR2 chemokine antagonists, Cyclic GMP phosphodiesterase inhibitors, Cyclooxygenase 2 inhibitors, Cyclooxygenase inhibitors, Cyclooxygenase stimulators, Cytochrome P450 3A4 inhibitors, Cytotoxic T-lymphocyte protein-4 stimulators, Dihydroceramide delta 4 desaturase inhibitors, Dihydroorotate dehydrogenase inhibitors, DNA polymerase inhibitors, DPP-4 inhibitors, EGFR family tyrosine kinase receptor modulators, Eosinophil peroxidase inhibitors, Eotaxin ligand inhibitors, EP4 prostanoid receptor agonists, Epidermal growth factor agonists, Epidermal growth factor ligands, Estrogen receptor beta agonists, Factor XIII agonists, FGF-10 ligands, FGF2 receptor agonists, Fractalkine ligand inhibitors, Free fatty acid receptor 2 antagonists, FXR agonists, GATA 3 transcription factor inhibitors, Glucagon-like peptide 1 agonists, Glucagon-like peptide 2 agonists, Glucocorticoid agonists, GM-CSF receptor agonists, G-protein coupled receptor 84 antagonists, Guanylate cyclase receptor agonists, Histamine H2 receptor antagonists, Histone acetyltransferase inhibitors, Histone deacetylase inhibitors, HLA class II antigen modulators, Hydrolase inhibitors, HSD17β13 inhibitors, ICAM1 gene inhibitors, ICAM-1 inhibitors, IL1 gene inhibitors, IL-10 agonists, IL10 gene stimulators, IL-11 agonists, IL-12 antagonists, IL12 gene inhibitors, IL-13 antagonists, IL-17 antagonists, IL-2 antagonists, IL-2 receptor alpha subunit inhibitors, IL-21 antagonists, IL-23 antagonists, IL-6 antagonists, IL6 gene inhibitors, IL-6 receptor modulators, IL-7 antagonists, IL-8 antagonists, Immunoglobulin G1 agonists, Immunoglobulin G2 modulators, Inosine monophosphate dehydrogenase inhibitors, Insulin sensitizers, Integrin alpha-4/beta-1 antagonists, Integrin alpha-4/beta-7 antagonists, Integrin alpha-E antagonists, Integrin antagonists, Integrin beta-7 antagonists, Interferon beta ligands, Interleukin 17E ligand inhibitors, Interleukin ligand inhibitors, Interleukin receptor 17A antagonists, Interleukin receptor 17B antagonists, Interleukin-1 beta ligands, Interleukin-1 beta ligand modulators, Interleukin-6 ligand inhibitors, JAK tyrosine kinase inhibitors, Jak1 tyrosine kinase inhibitors, JAK2 gene inhibitors, Jak3 tyrosine kinase inhibitors, Jun N terminal kinase inhibitors, LanC like protein 2 modulators, Leukotriene BLT receptor antagonists, Lipoxygenase modulators, L-Selectin antagonists, MAdCAM inhibitors, Matrix metalloprotease inhibitors, Matrix metalloprotease modulators, Melanocortin agonists, Membrane copper amine oxidase inhibitors, Metalloprotease-2 inhibitors, Metalloprotease-9 inhibitors, MIP 3 alpha ligand inhibitors, Mitochondrial 10 kDa heat shock protein stimulators, Monocyte differentiation antigen CD14 inhibitors, mTOR inhibitors, Mucin stimulators, NAD-dependent deacetylase sirtuin-1 stimulators, Natriuretic peptide receptor C agonists, Neuregulin-4 ligands, Nicotinic acetylcholine receptor agonists, Nicotinic ACh receptor alpha 4 subunit modulators, Nicotinic ACh receptor alpha 7 subunit stimulators, Nicotinic ACh receptor beta 2 subunit modulators, NK1 receptor antagonists, NKG2 D activating NK receptor antagonists, Nuclear factor kappa B inhibitors, Opioid growth factor receptor agonists, Opioid receptor antagonists, Opioid receptor delta antagonists, Oxidoreductase inhibitors, P2X7 purinoceptor agonists, p38 MAP kinase inhibitors, PARP inhibitors, PDE 4 inhibitors, PDGF receptor agonists, Phagocytosis stimulating peptide modulators, Phospho MurNAc pentapeptide transferase inhibitors, Phospholipase A2 inhibitors, Platelet activating factor receptor antagonists, Potassium channel inhibitors, PPAR alpha agonists, PPAR delta agonists, PPAR gamma agonists, Protein CYR61 stimulators, Protein fimH inhibitors, Protein kinase C alpha inhibitors, Protein kinase C beta inhibitors, Protein kinase C delta inhibitors, Protein kinase C epsilon inhibitors, Protein kinase C eta inhibitors, Protein kinase C. theta inhibitors, Protein kinase G inhibitors, Protein kinase inhibitors, P-selectin glycoprotein ligand-1 inhibitors, PurH purine biosynthesis protein inhibitors, Retinoic acid receptor alpha agonists, Retinoic acid receptor beta agonists, Retinoid receptor agonists, RNA polymerase inhibitors, SMAD-7 inhibitors, Sodium channel inhibitors, Somatostatin receptor agonists, Sphingosine 1 phosphate phosphatase 1 stimulators, Sphingosine 1 phosphate phosphatase modulators, Sphingosine kinase 1 inhibitors, Sphingosine kinase 2 inhibitors, Sphingosine-1-phosphate receptor-1 agonists, Sphingosine-1-phosphate receptor-1 antagonists, Sphingosine-1-phosphate receptor-1 modulators, Sphingosine-1- phosphate receptor-5 modulators, STAT3 gene inhibitors, STAT-3 inhibitors, STAT-4 inhibitors, Stem cell antigen-1 inhibitors, Superoxide dismutase modulators, Superoxide dismutase stimulators, SYK kinase inhibitors, T cell surface glycoprotein CD28 inhibitors, TGF beta 1 ligand inhibitors, Thymulin agonists, THR-β agonists, TLR-2 antagonists, TLR-4 antagonists, TLR-9 agonists, TNF alpha ligand inhibitors, TNF alpha ligand modulators, TNF antagonists, TPL2 kinase inhibitors, Trefoil factor modulators, Tryptase inhibitors, Tryptophan 5-hydroxylase inhibitors, Tumor necrosis factor 14 ligand modulators, TYK2 kinase inhibitors, Type I TNF receptor antagonists, Type II TNF receptor modulators, Unspecified growth factor receptor modulators, Vanilloid VR1 agonists, Vitamin D3 receptor agonists, Zonulin inhibitors, abatacept; acemannan; adalimumab; DCCT-10; apremilast; AST-120; balsalazide; balsalazide sodium; basiliximab; beclomethasone dipropionate; budesonide; D-9421; budesonide MMX; catridecacog; certolizumab pegol; *Clostridium butyricum*; etanercept; fingolimod; glatiramer acetate; golimumab; infliximab; infliximab biosimilar; infliximab follow-on biologic; interferon beta-la; lenalidomide; mesalazine; GED-0001; AJG-501; metenkefalin acetate with tridecactide acetat, mycophenolate mofetil; naltrexone; natalizumab; nitazoxanide; olsalazine; oprelvekin; propionyl-L-carnitine; recombinant interferon beta-la; remestemcel-L; rifaximin; rituximab; ropivacaine; rosiglitazone; sargramostim; secukinumab; SPD-480; tacrolimus; tamibarotene; teduglutide; thalidomide; tocilizumab; RO-4877533; tofacitinib; CP-690550; *Trichuris suis* ova; ASP-1002; ustekinumab; valganciclovir; vedolizumab; zileuton; anti-CD3 imaging agent (antibody fragment, cancer/autoimmune disease), ImaginAb; AVX-470; ciclosporin; CXCR1/2 ligands mAb (immunology), Eli Lilly; FFP-102; GSK-3050002; INN-108; IR-777; SGM-1019; peg-ilodecakin; PF-06480605; PF-06651600; SER-287; Syn-1002; Thetanix; tolerogenic dendritic cell therapy TOP-1288; VBY-036; VBY-129; 946414-98-8; BMS-936557; 99mTc-annexin V-128; ABC-294640; abrilumab; Alequel; AMG-139; amiselimod; APD-334; ASP-3291; beclomethasone dipropionate; bertilimumab; ciclosporin; clazakizumab; DLX-105; dolcanatide; E-6011; ETX-201; FFP-104; filgotinib; foralumab; GED-0507-34-Levo; givinostat; GLPG-0974; GLPG-1205; iberogast N (ulcerative colitis), Bayer; BAY98-7410; INV-103; JNJ-40346527; K(D)PT; KAG-308; KHK-4083; KRP-203; larazotide acetate; CB-01-05-MMX; LY-3074828; mesalamine with N-acetylcysteine; midismase; molgramostim follow on biologic with fosfomycin with carbapenem, Reponex; multipotent adult progenitor cell therapy (ischemia/cerebral palsy), Athersys/Healios; NN-8828; olokizumab; OvaSave; P-28-GST; PDA-002; PF-4236921; PF-547659; prednisolone; PUR-0110; QBECO; RBX-2660; repurposed naltrexone; JKB-122; SB-012; sotrastaurin; STNM-01; TAK-114; tetomilast; Debio-0512; TRK-170; TRX-318; vatelizumab; VB-201; ZP-1848; zucapsaicin; ABT-494; alicaforsen; Ampion; BI-655066; briakinumab; cannabidiol; carotegast methyl; cobitolimod; dexamethasone sodium phosphate; elafibranor; etrolizumab; GS-5745; HMPL-004; LP-02; mesalazine; metronidazole mongersen; ocrelizumab; ozanimod; peficitinib; RHB-104; rifaximin; tildrakizumab; tralokinumab; brodalumab; laquinimod; plecanatide; telotristat etiprate; infliximab biosimilar, Samsung Bioepis; AZD-058; and rifabutin with clarithromycin and further with clofazimine.

Also, the following non-exhaustive list of classes of compounds and compounds may be combined with a compound of the present disclosure: 5-Lipoxygenase inhibitors, such as zileuton, etalocibm FPL-64170, E-3040, and BU-4601A; Acetylcholinesterase inhibitors, such as BL-7040; ACTH receptor agonists, such as metenkefalin acetate with tridecactide acetate, and FAR-404; Activin receptor antagonists such as follistatin; Acyltransferase inhibitors such as AZD-0585; Adrenocorticotrophic hormone ligands, such as metenkefalin acetate with tridecactide acetate, and FAR-404; AKT1 gene inhibitors, such as vidofludimus; Alkaline phosphatase modulators such as recombinant human alkaline phosphatase (oral, ulcerative colitis), AM-Pharma; Alkaline phosphatase stimulators such as bovine alkaline phosphatase; Androgen receptor agonists, such as PB-005; Apolipoprotein C3 antagonists, such as AZD-0585; Bactericidal permeability protein stimulators, such as opebacan; Beta adrenoceptor antagonists, such as NM-001; Beta-glucuronidase inhibitors, such as KD-018; B-lymphocyte antigen CD20 inhibitors, such as ocrelizumab, rituximab; Bradykinin receptor modulators, such as givinostat; Calcineurin inhibitors, such as tacrolimus, ciclosporin; Calcium channel inhibitors, such as clotrimazole; Cannabinoid CB1 receptor modulators, such as GWP42003-P, cannabidiol; Cannabinoid CB2 receptor modulators, such as GWP42003-P, cannabidiol; Cannabinoid receptor antagonists, such as fingolimod; Cannabinoid receptor modulators, such as GWP42003-P, cannabidiol; Cathepsin S inhibitors, such as VBY-129, VBY-036; CCN protein stimulators, such as CSA-13; CCR3 chemokine antagonists, such as bertilimumab; CCR5 chemokine antagonists, such as HGS-1025; CCR9 chemokine antagonists, such as MLN-3126, vercirnon, CCX-025; CD3 modulators, such as visilizumab; CD40 ligand inhibitors, such as FFP-104; CD40 ligand receptor antagonists, such as FFP-104, FFP-102, toralizumab; CD49b antagonists, such as vatelizumab; CD49d antagonists, such as ELND-004; CD89 agonists, such as HF-1020; Cell adhesion molecule inhibitors, such as natalizumab, alicaforsen (intravenous), ASP-2002, ISIS-2302; Chemokine CXC ligand inhibitors, such as CXCR1/2 ligands mAb (immunology), Eli Lilly; CHST15 gene inhibitors, such as STNM-01; Collagen modulators, such as adipose-derived stem cell therapy (Celution System), Cytori, DCCT-10; CSF-1 agonists, such as sargramostim, molgramostim follow on biologic with fosfomycin with carbapenem (intraintestinal, Crohn's disease), Reponex; CSF-1 antagonists, such as JNJ-40346527; CXC10 chemokine ligand inhibitors, such as 946414-98-8, BMS-936557; CXCR2 chemokine antagonists, such as elubrixin; Cyclic GMP phosphodiesterase inhibitors, such as CEL-031; Cyclooxygenase 2 inhibitors, such as P-54; Cyclooxygenase inhibitors, such as mesalazine, 4-aminosalicylate sodium, AJG-501, AGI-022; Cyclooxygenase stimulators, such as nicotine polacrilex; Cytochrome P450 3A4 inhibitors, such as KD-018; Cytotoxic T-lymphocyte protein-4 stimulators, such as abatacept; Dihydroceramide delta 4 desaturase inhibitors, such as ABC-294640; Dihydroorotate dehydrogenase inhibitors, such as vidofludimus; DNA polymerase inhibitors, such as valganciclovir; EGFR family tyrosine kinase receptor modulators, such as neuregulin 4 (Crohn's disease/ulcerative colitis/necrotizing enterocolitis), Avexegen Therapeutics/Children's Hospital of Los Angeles; Eosinophil peroxidase inhibitors, such as AWEPOPD-01, AWEPO-003; Eotaxin ligand inhibitors, such as bertilimumab; EP4 prostanoid receptor agonists, such as KAG-308; Epidermal growth factor agonists, such as heparin-EGF-like factor, Scios Nova; Epidermal growth factor ligands, such as Hebervis; Estrogen receptor beta agonists, such as prinaberel; Factor XIII agonists, such as catridecacog; FGF-10 ligands, such as repifermin; FGF2 receptor agonists, such as F2A; Fractalkine ligand inhibitors, such as E-6011; Free fatty acid receptor 2 antagonists, such as GLPG-0974; GATA 3 transcription factor inhibitors, such as SB-012; Glucagon-like peptide 2 agonists, such as teduglutide, ZP-1848, NB-1002; Glucocorticoid agonists, such as budesonide, beclomethasone dipropionate, dexamethasone sodium phosphate, AJG-511, DOR-201, D-9421-C; GM-CSF receptor agonists, such as sargramostim, molgramostim follow on biologic with fosfomycin with carbapenem (intraintestinal, Crohn's disease), Reponex; G-protein coupled receptor 84 antagonists, such as GLPG-1205; Guanylate cyclase receptor agonists, such as dolcanatide, SP-333; Histamine H2 receptor antagonists, such as bismuth, Medeva; Histone acetyltransferase inhibitors, such as TIP60 inhibitors (ulcerative colitis/inflammatory bowel disease/autoimmune diseases), University of Pennsylvania; Histone deacetylase inhibitors, such as givinostat; HLA class II antigen modulators, such as HLA class II protein modulators (Crohns disease), Nextera AS; Hydrolase inhibitors, such as SC-56938; ICAM1 gene inhibitors, such as alicaforsen; ICAM-1 inhibitors, such as alicaforsen (intravenous), ISIS-2302; IL1 gene inhibitors, such as PLR-14; IL-10 agonists, such as peg-ilodecakin, AM-0010; IL10 gene stimulators, such as gene therapy (IL-10), Imperial College; IL-11 agonists, such as oprelvekin, YM-294; IL-12 antagonists, such as ustekinumab, briakinumab, apilimod; IL12 gene inhibitors, such as RDP-58; IL-13 antagonists, such as tralokinumab, anrukinzumab; IL-17 antagonists, such as secukinumab, vidofludimus; IL-2 antagonists, such as daclizumab; IL-2 receptor alpha subunit inhibitors, such as basiliximab, daclizumab, BSX-003, Ro-34-7375; IL-21 antagonists, such as NN-8828, ATR-107; IL-23 antagonists, such as tildrakizumab, ustekinumab, BI-655066, AMG-139, briakinumab, LY-3074828, apilimod; IL-6 antagonists, such as tocilizumab, clazakizumab, olokizumab, HMPL-004, AMG-220, FM-101; IL6 gene inhibitors, such as YSIL6-T-PS; IL-6 receptor modulators, such as tocilizumab; IL-7 antagonists, such as interleukin-7 receptor modulators (ulcerative colitis/T-cell acute lymphoblastic leukaemia), Effimune; IL-8 antagonists, such as elubrixin, clotrimazole; Immunoglobulin G1 agonists, such as HF-1020; Immunoglobulin G2 modulators, such as PF-547659; Inosine monophosphate dehydrogenase inhibitors, such as mycophenolate mofetil; Insulin sensitizers, such as elafibranor, rosiglitazone, HE-3286, EGS-21; Integrin alpha-4/beta-1 antagonists, such as natalizumab, TRK-170, firategrast; Integrin alpha-4/beta-7 antagonists, such as etrolizumab, vedolizumab, abrilumab, carotegast methyl, TRK-170, firategrast; Integrin alpha-E antagonists, such as etrolizumab; Integrin antagonists, such as vatelizumab, ASP-2002; Integrin beta-7 antagonists, such as etrolizumab; Interferon beta ligands, such as interferon beta-la, recombinant interferon beta-la, Serono; Interleukin 17E ligand inhibitors, such as anti-IL-17BR humanized antibody (lung fibrosis/asthma/ulcerative colitis), Medical Research Council Technology; Interleukin ligand inhibitors, such as HE-3286; Interleukin receptor 17A antagonists, such as brodalumab; Interleukin receptor 17B antagonists, such as anti-IL-17BR humanized antibody (lung fibrosis/asthma/ulcerative colitis), Medical Research Council Technology; Interleukin-1 beta ligands, such as K(D)PT, PUR-0110, HMPL-004; Interleukin-1 beta ligand modulators, such as PUR-0110, HMPL-004; Interleukin-6 ligand inhibitors, such as PF-4236921; JAK tyrosine kinase inhibitors, such as tofacitinib, peficitinib; Jak1 tyrosine kinase inhibitors, such as ABT-494, tofacitinib, filgotinib, peficitinib, GLPG-0555, solcitinib; JAK2 gene inhibitors, such as vidofludimus; Jak3 tyrosine kinase inhibitors, such as tofacitinib, peficitinib; Jun N terminal kinase inhibitors, such as semapimod; LanC like protein 2 modulators, such as BT-11; Leukotriene BLT receptor antagonists, such as ONO-4057, etalocib, SC-53228, SC-52798; Lipoxygenase modulators, such as mesalazine; L-Selectin antagonists, such as BNP-001; MAdCAM inhibitors, such as vedolizumab, PF-547659; Matrix metalloprotease inhibitors, such as D-5410; Matrix metalloprotease modulators, such as D-5410; Melanocortin agonists, such as ASP-3291; Membrane copper amine oxidase inhibitors, such as vepalimomab; Metalloprotease-2 inhibitors, such as KD-018, RWJ-68354; Metalloprotease-9 inhibitors, such as GS-5745; MIP 3 alpha ligand inhibitors, such as GSK-3050002; Mitochondrial 10 kDa heat shock protein stimulators, such as INV-103; Monocyte differentiation antigen CD14 inhibitors, such as CD14 anti-inflammatory, Cornell; mTOR inhibitors, such as P-2281; Mucin stimulators, such as rebamipide; NAD-dependent deacetylase sirtuin-1 stimulators, such as SRT-2104; Natriuretic peptide receptor C agonists, such as plecanatide; Neuregulin-4 ligands, such as neuregulin 4 (Crohn's disease/ulcerative colitis/necrotizing enterocolitis), Avexegen Therapeutics/Children's Hospital of Los Angeles; Nicotinic acetylcholine receptor agonists, such as TC-2403, nicotine polacrilex, nicotine; Nicotinic ACh receptor alpha 4 subunit modulators, such as TC-2403; Nicotinic ACh receptor alpha 7 subunit stimulators, such as GTS-21; Nicotinic ACh receptor beta 2 subunit modulators, such as TC-2403; NK1 receptor antagonists, such as KD-018, nolpitantium besilate; NKG2 D activating NK receptor antagonists, such as NNC-0142-002; Nuclear factor kappa B inhibitors, such as KD-018, cobitolimod, CSA-13, HE-3286, HMPL-004, Avrina, mesalamine with N-acetylcysteine, P-54; Opioid growth factor receptor agonists, such as metenkefalin acetate with tridecactide acetate, FAR-404; Opioid receptor antagonists, such as naltrexone, IRT-103; Opioid receptor delta antagonists, such as KD-018; Oxidoreductase inhibitors, such as olsalazine; P2X7 purinoceptor agonists, such as givinostat; p38 MAP kinase inhibitors, such as RDP-58, doramapimod, semapimod, RWJ-68354; PARP inhibitors, such as EB-47, INO-1003; PDE 4 inhibitors, such as apremilast, tetomilast, CC-1088; PDGF receptor agonists, such as oprelvekin, YM-294; Phagocytosis stimulating peptide modulators, such as 99mTc-RP-128; Phospho MurNAc pentapeptide transferase inhibitors, such as SQ-641; Phospholipase A2 inhibitors, such as varespladib methyl; Platelet activating factor receptor antagonists, such as dersalazine sodium; Potassium channel inhibitors, such as clotrimazole; PPAR alpha agonists, such as elafibranor (GFT-1007); PPAR delta agonists, such as elafibranor (GFT-1007); PPAR gamma agonists, such as rosiglitazone, GED-0507-34-Levo, etalocib; Protein CYR61 stimulators, such as CSA-13; Protein fimH inhibitors, such as EB-8018; Protein kinase C alpha inhibitors, such as sotrastaurin (AEB-071); Protein kinase C beta inhibitors, such as sotrastaurin (AEB-071); Protein kinase C delta inhibitors, such as sotrastaurin (AEB-071); Protein kinase C epsilon inhibitors, such as sotrastaurin (AEB-071); Protein kinase C eta inhibitors, such as sotrastaurin (AEB-071); Protein kinase C. theta inhibitors, such as sotrastaurin (AEB-071); Protein kinase G inhibitors, such as CEL-031; Protein kinase inhibitors, such as TOP-1288; P-selectin glycoprotein ligand-1 inhibitors, such as SEL-K2; PurH purine biosynthesis protein inhibitors, such as mycophenolate mofetil; Retinoic acid receptor alpha agonists, such as tamibarotene; Retinoic acid receptor beta agonists, such as tamibarotene; Retinoid receptor agonists, such as tamibarotene; RNA polymerase inhibitors, such as rifaximin; SMAD-7 inhibitors, such as mongersen (GED-0301); Sodium channel inhibitors, such as ropivacaine; Somatostatin receptor agonists, such as vapreotide; Sphingosine 1 phosphate phosphatase 1 stimulators, such as APD-334; Sphingosine 1 phosphate phosphatase modulators, such as SIP modulators (oral, multiple sclerosis/ulcerative colitis/rheumatoid arthritis), Akaal Pharma; Sphingosine kinase 1 inhibitors, such as ABC-294640; Sphingosine kinase 2 inhibitors, such as ABC-294640; Sphingosine-1-phosphate receptor-1 agonists, such as ozanimod (RPC-1063), KRP-203; Sphingosine-1-phosphate receptor-1 antagonists, such as amiselimod (MT-1303); Sphingosine-1-phosphate receptor-1 modulators, such as fingolimod (FTY-720), ozanimod (RPC-1063), amiselimod (MT-1303); Sphingosine-1-phosphate receptor-5 modulators, such as ozanimod; STAT3 gene inhibitors, such as vidofludimus; STAT-3 inhibitors, such as TAK-114; STAT-4 inhibitors, such as STAT-4 antisense oligonucleotide (Crohns disease/colitis), NIAID; Stem cell antigen-1 inhibitors, such as Ampion, DMI-9523; Superoxide dismutase modulators, such as midismase, LT-0011; Superoxide dismutase stimulators, such as superoxide dismutase; T cell surface glycoprotein CD28 inhibitors, such as abatacept; TGF beta 1 ligand inhibitors, such as mongersen, GED-0301; Thymulin agonists, such as Syn-1002; TLR-2 antagonists, such as VB-201; TLR-4 antagonists, such as JKB-122, VB-201; TLR-9 agonists, such as BL-7040, cobitolimod; TNF alpha ligand inhibitors, such as adalimumab, certolizumab pegol, infliximab biosimilar, infliximab, golimumab, ISIS-104838, CSA-13, DLX-105, adalimumab biosimilar, dersalazine sodium, Debio-0512, HMPL-004, DLX-105, infliximab follow-on biologic, AZD-9773, CYT-020-TNFQb, DOM-0200; TNF alpha ligand modulators, such as PUR-0110, CDP-571; TNF antagonists, such as etanercept, certolizumab pegol, AVX-470, onercept; Trefoil factor modulators, such as AG-012; Tryptase inhibitors, such as APC-2059; Tryptophan 5-hydroxylase inhibitors, such as telotristat etiprate; Tumor necrosis factor 14 ligand modulators, such as SAR-252067; Type I TNF receptor antagonists, such as DOM-0100; Type II TNF receptor modulators, such as etanercept; Unspecified growth factor receptor modulators, such as AP-005; Vanilloid VR1 agonists, such as zucapsaicin; Vitamin D3 receptor agonists, such as calcitriol; and Zonulin inhibitors, such as larazotide acetate, AT-1001.

Also, the following non-exhaustive list of classes of compounds and compounds may be combined with a compound of the present disclosure: 14-3-3 protein eta inhibitors, 5-Lipoxygenase inhibitors, Abl tyrosine kinase inhibitors, ACTH receptor agonists, Adenosine A3 receptor agonists, Adenosine deaminase inhibitors, ADP ribosyl cyclase-1 modulators, ADP ribosylation factor 6 inhibitors, Adrenocorticotrophic hormone ligands, Aggrecanase-2 inhibitors, Albumin modulators, AP1 transcription factor inhibitors, Basigin inhibitors, Bcr protein inhibitors, B-lymphocyte antigen CD19 inhibitors, B-lymphocyte antigen CD20 inhibitors, B-lymphocyte antigen CD20 modulators, B-lymphocyte stimulator ligand inhibitors, Bradykinin receptor modulators, BRAF gene inhibitors, Branched amino acid aminotransferase 1 inhibitors, Bromodomain containing protein inhibitors, Btk tyrosine kinase inhibitors, Cadherin-11 antagonists, Calcineurin inhibitors, Calcium channel inhibitors, Carbonic anhydrase inhibitors, Cathepsin K inhibitors, Cathepsin S inhibitors, CCR1 chemokine antagonists, CCR2 chemokine antagonists, CCR3 gene modulators, CCR5 chemokine antagonists, CD126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, Cell adhesion molecule inhibitors, Choline kinase inhibitors, Clusterin stimulators, Complement C5 factor inhibitors, Complement Factor stimulators, C-reactive protein inhibitors, CSF-1 antagonists, CXC10 chemokine ligand inhibitors, CXCR4 chemokine antagonists, Cyclin-dependent kinase inhibitor 1 inhibitors, Cyclin-dependent kinase-2 inhibitors, Cyclin-dependent kinase-4 inhibitors, Cyclin-dependent kinase-5 inhibitors, Cyclin-dependent kinase-6 inhibitors, Cyclin-dependent kinase-7 inhibitors, Cyclin-dependent kinase-9 inhibitors, Cyclooxygenase 2 inhibitors, Cyclooxygenase 2 modulators, Cyclooxygenase inhibitors, Cytosolic phospholipase A2 inhibitors, Cytotoxic T-lymphocyte protein-4 modulators, Cytotoxic T-lymphocyte protein-4 stimulators, DHFR inhibitors, Diamine acetyltransferase inhibitors, Dihydroorotate dehydrogenase inhibitors, Elongation factor 2 inhibitors, Eotaxin 2 ligand inhibitors, EP4 prostanoid receptor antagonists, Erythropoietin receptor agonists, Fas ligands, FGF-2 ligand inhibitors, FK506 binding protein-12 modulators, Folate antagonists, Folate receptor agonists, Folate receptor beta antagonists, Folate receptor modulators, Fractalkine ligand inhibitors, Fyn tyrosine kinase inhibitors, G protein coupled receptor 15 antagonists, GABA A receptor modulators, Glucocorticoid agonists, Glucocorticoid antagonists, Glucocorticoid induced leucine zipper stimulators, GM-CSF ligand inhibitors, GM-CSF receptor antagonists, GM-CSF receptor modulators, Growth regulated protein alpha ligand inhibitors, Hwith Kwith ATPase inhibitors, Histamine H4 receptor antagonists, Histone deacetylase inhibitors, Histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, Hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-2 agonists, IL-2 antagonists, IL-21 antagonists, IL-23 antagonists, IL-3 antagonists, IL-4 agonists, IL-6 antagonists, IL-6 receptor modulators, Immunoglobulin antagonists, Immunoglobulin G1 agonists, Immunoglobulin G1 antagonists, Immunoglobulin G1 modulators, Immunoglobulin G2 antagonists, Immunoglobulin G2 modulators, Immunoglobulin gamma Fc receptor II modulators, Immunoglobulin gamma Fc receptor IIB antagonists, Immunoglobulin kappa modulators, Immunoglobulin M antagonists, Inducible nitric oxide synthase inhibitors, Inosine monophosphate dehydrogenase inhibitors, Insulin sensitizers, Integrin alpha-1/beta-1 antagonists, Integrin alpha-4/beta-1 antagonists, Integrin antagonists, Interferon beta ligands, Interferon gamma ligands, Interleukin 17A ligand inhibitors, Interleukin 17F ligand inhibitors, Interleukin 23A inhibitors, Interleukin ligands, Interleukin receptor 17A antagonists, Interleukin-1 beta ligand inhibitors, Interleukin-10 ligands, Interleukin-2 ligands, Interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-3 modulators, Kelch like ECH associated protein 1 modulators, Kit tyrosine kinase inhibitors, LanC like protein 2 modulators, LITAF gene inhibitors, Lymphocyte function antigen-3 receptor antagonists, Lyn tyrosine kinase inhibitors, Macrophage mannose receptor 1 modulators, MAdCAM inhibitors, MAP kinase modulators, MAP3K2 gene inhibitors, MAPKAPK5 inhibitors, Matrix metalloprotease inhibitors, MCL1 gene inhibitors, MEK protein kinase inhibitors, MEK-1 protein kinase inhibitors, MEK-2 protein kinase inhibitors, Membrane copper amine oxidase inhibitors, Metalloprotease-2 inhibitors, Metalloprotease-9 inhibitors, Midkine ligand inhibitors, Mitochondrial 10 kDa heat shock protein stimulators, mTOR complex 1 inhibitors, mTOR inhibitors, NAD ADP ribosyltransferase stimulators, NAMPT gene inhibitors, NF kappa B inhibitor stimulators, NFAT gene inhibitors, NFE2L2 gene stimulators, Nicotinic acetylcholine receptor antagonists, NK cell receptor modulators, NKG2 A B activating NK receptor antagonists, NKG2 D activating NK receptor antagonists, Nuclear erythroid 2-related factor 2 stimulators, Nuclear factor kappa B inhibitors, Nuclear factor kappa B modulators, Nuclear factor kappa B p105 inhibitors, Opioid growth factor receptor agonists, Opioid receptor delta antagonists, Osteoclast differentiation factor antagonists, Osteoclast differentiation factor ligand inhibitors, Oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, Phosphoinositide-3 kinase delta inhibitors, Phosphoinositide-3 kinase gamma inhibitors, Phospholipase A2 inhibitors, Platelet activating factor receptor antagonists, PPAR gamma agonists, Programmed cell death protein 1 modulators, Prostaglandin D synthase stimulators, Protein arginine deiminase inhibitors, Protein tyrosine kinase inhibitors, PurH purine biosynthesis protein inhibitors, Rho associated protein kinase 2 inhibitors, Seprase inhibitors, Signal transducer CD24 modulators, Signal transduction inhibitors, Sodium glucose transporter-2 inhibitors, Sphingosine 1 phosphate phosphatase modulators, STAT3 gene inhibitors, Superoxide dismutase stimulators, SYK family tyrosine kinase inhibitors, Syk tyrosine kinase inhibitors, Syndecan-1 inhibitors, T cell receptor antagonists, T cell receptor modulators, T cell surface glycoprotein CD28 inhibitors, T cell surface glycoprotein CD28 stimulators, TAK1 binding protein modulators, Talin modulators, T-cell differentiation antigen CD6 inhibitors, T-cell surface glycoprotein CD8 inhibitors, Tenascin modulators, TGF beta agonists, Thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, Transcription factor p65 inhibitors, Transcription factor RelB inhibitors, Transferrin modulators, Tumor necrosis factor 13C receptor antagonists, Tumor necrosis factor 15 ligand inhibitors, Tumor necrosis factor ligand 13 inhibitors, Tumor necrosis factor ligand inhibitors, Type I IL-1 receptor antagonists, Type I TNF receptor antagonists, Type II TNF receptor modulators, Unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, Zap70 tyrosine kinase inhibitors, 99mTc labelled annexin V-128, abatacept, abatacept biosimilar, ABBV-257, ABT-122, ABT-494, acalabrutinib, aceclofenac, actarit, MS-392, adalimumab, adalimumab biosimilar, adalimumab follow-on biologic, AK-106, ALX-0061, aminopterin, anakinra, anakinra biosimilar, anakinra follow-on biologic, ARG-301, ASLAN-003, ASP-5094, AT-132, AZD-9567, baricitinib, BI-655064, bimekizumab, BiP (rheumatoid arthritis), Kings College London, BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, Mallinckrodt, CR-6086, CreaVax-RA, CWG-92, CWG-940, Cx-611, DE-098, deflazacort, Rheumavax, denosumab, diacerein, diclofenac, E-6011, eicosapentaenoic acid monoglycerides, etanercept, etanercept biosimilar, etanercept follow-on biologic, etodolac, etoricoxib, filgotinib, fosdagrocorat, gerilimzumab, ginsenoside C-K, givinostat, goat polyclonal antibodies, golimumab, GS-5745, GS-9876, GSK-3196165, HM-71224, HMPL-523, hyaluronate sodium, IB-RA (injectable, rheumatoid arthritis), Innobioscience, IB-RA (oral, rheumatoid arthritis), Innobioscience, iguratimod, IMD-2560, imidazole salicylate, infliximab, infliximab biobetter, infliximab biosimilar, INSIX RA, interferon gamma follow-on biologic, interleukin-2 (injectable), interleukin-2 follow-on biologic, INV-103, IR-501, itolizumab, JNJ-40346527, Ka Shu Ning, KD-025, ketoprofen with omeprazole, leflunomide, lenzilumab, LLDT-8, lumiracoxib, LY-3090106, masitinib, mavrilimumab, MBS-2320, MEDI-5117, meloxicam, methotrexate, MGD-010, misoprostol with diclofenac, MM-A01-01, monalizumab, MORAb-022, MPC-300-IV, MRC-375, nabumetone, namilumab, naproxen with esomeprazole, naproxen with esomeprazole strontium, ocaratuzumab, ofatumumab, OHR-118, olokizumab, OM-89, once-daily naproxen (oral controlled release, pain), Alvogen, ONO-4059, Oralgam, ozoralizumab, peficitinib, pelubiprofen, PF-06687234, piperidone hydrochloridum, piroxicam, prednisolone, prednisone, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), recombinant human interleukin-1 receptor antagonist (rheumatoid arthritis), Shanghai Fudan-Zhangjiang Bio-Pharmaceutical, recombinant human interleukin-2 recombinant TNF receptor 2-Fc fusion protein mutant, RG-6125, RhuDex, rifabutin with clarithromycin with clofazimine, rituximab, rituximab biosimilar, rituximab follow-on biologic, RPI-78, SAN-300, sarilumab, SBI-087, seliciclib, SHR-0302, sirukumab, spebrutinib, SSS-07, KDDF-201110-06, Syn-1002, T-5224, TAB-08, tacrolimus, TAK-020, TAK-079, tarenflurbil (transdermal spraygel, skin disease/rheumatoid arthritis), MIKA Pharma/GALENpharma, technetium Tc 99m tilmanocept, technetium[99Tc] methylenediphosphonate, tenoxicam, Debio-0512, tocilizumab, tofacitinib, *Trichuris suis* ova, umbilical cord-derived mesenchymal stem cells (iv, RA/liver disease), Alliancells/Zhongyuan Union, ustekinumab, VAY-736, VB-201, WF-10, XmAb-5871, YHB-1411-2; 14-3-3 protein eta inhibitors, such as anti-AGX-020 mAbs (rheumatoid arthritis), Augurex; 5-Lipoxygenase inhibitors, such as tenoxicam, darbufelone, tebufelone, licofelone, ZD-2138, etalocib, tenidap, tepoxalin, flobufen, SKF-86002, PGV-20229, L-708780, WY-28342, T-0757, T-0799, ZM-216800, L-699333, BU-4601A, SKF-104351, CI-986; Abl tyrosine kinase inhibitors, such as imatinib; ACTH receptor agonists, such as FAR-404, metenkefalin acetate with tridecactide acetate; Adenosine A3 receptor agonists, such as CF-101; Adenosine deaminase inhibitors, such as cladribine, pentostatin, FR-221647; ADP ribosyl cyclase-1 modulators, such as indatuximab ravtansine; ADP ribosylation factor 6 inhibitors, such as NAV-2729; Adrenocorticotrophic hormone ligands, such as corticotropin, Mallinckrodt, FAR-404, metenkefalin acetate with tridecactide acetate; Aggrecanase-2 inhibitors, such as GIBH-R-001-2; Albumin modulators, such as ALX-0061, ONS-1210; AP1 transcription factor inhibitors, such as T-5224, tarenflurbil, SP-10030; Basigin inhibitors, such as ERG-240; Bcr protein inhibitors, such as imatinib; B-lymphocyte antigen CD19 inhibitors, such as XmAb-5871, MDX-1342; B-lymphocyte antigen CD20 inhibitors, such as ocrelizumab, ofatumumab, rituximab, rituximab biosimilar, veltuzumab, rituximab follow-on biologic, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101; B-lymphocyte antigen CD20 modulators, such as rituximab biosimilar, SBI-087, TRU-015, DXL-625; B-lymphocyte stimulator ligand inhibitors, such as belimumab, RCT-18, blisibimod, tabalumab, atacicept, briobacept; Bradykinin receptor modulators, such as givinostat; BRAF gene inhibitors, such as binimetinib; Branched amino acid aminotransferase 1 inhibitors, such as ERG-240; Bromodomain containing protein inhibitors, such as RVX-297, ZEN-003694; Btk tyrosine kinase inhibitors, such as acalabrutinib, HM-71224, spebrutinib, BTK inhibitor (rheumatoid arthritis), Humanwell Healthcare/Wuxi AppTech, BMS-986142, TAK-020, ONO-4059, TAS-5315, ABBV-105, AC-0025, RN-486, CG-026806, GDC-0834; Cadherin-11 antagonists, such as RG-6125; Calcineurin inhibitors, such as HS-378, ciclosporin; Calcium channel inhibitors, such as RP-3128; Carbonic anhydrase inhibitors, such as polmacoxib; Cathepsin K inhibitors, such as CRA-013783, T-5224, AM-3876, VEL-0230, NPI-2019; Cathepsin S inhibitors, such as MIV-247, AM-3876, RWJ-445380, NPI-2019; CCR1 chemokine antagonists, such as BX-471, BMS-817399, BI-638683, CCX-354, MLN-3701, MLN-3897, CP-481715, PS-375179; CCR2 chemokine antagonists, such as MK-0812, AZD-6942; CCR3 gene modulators, such as CM-102; CCR5 chemokine antagonists, such as maraviroc, OHR-118, NIBR-6465, AZD-5672, AZD-8566; CD126 antagonists, such as sarilumab; CD29 modulators, such as PF-06687234; CD3 modulators, such as otelixizumab; CD39 agonists, such as AAVS-CD39/CD73 (rheumatoid arthritis), Arthrogen; CD4 agonists, such as maraviroc; CD4 antagonists, such as tregalizumab, zanolimumab, MTRX-1011A, BW-4162W94, EP-1645, clenoliximab; CD40 ligand inhibitors, such as dapirolizumab pegol; CD40 ligand receptor antagonists, such as BI-655064, anti-CD40-XTEN, teneliximab; CD40 ligand receptor modulators, such as CFZ-533; CD52 antagonists, such as alemtuzumab; CD73 agonists, such as AAVS-CD39/CD73 (rheumatoid arthritis), Arthrogen; CD79b modulators, such as MGD-010; CD80 antagonists, such as RhuDex, XENP-9523, ASP-2408, abatacept biobetter; CD86 antagonists, such as ES-210, abatacept biosuperior, ASP-2408, XENP-9523; CD95 antagonists, such as DE-098, CS-9507; Cell adhesion molecule inhibitors, such as natalizumab, alicaforsen, NPC-17923, TK-280, PD-144795; Choline kinase inhibitors, such as choline kinase inhibitors (rheumatoid arthritis), UC San Diego; Clusterin stimulators, such as alemtuzumab; Complement C5 factor inhibitors, such as eculizumab, antisense oligonucleotides (rheumatoid arthritis), Leiden University Medical Center; Complement Factor stimulators, such as CM-101; C-reactive protein inhibitors, such as IB-RA (oral, rheumatoid arthritis), Innobioscience, ISIS-353512; CSF-1 antagonists, such as masitinib, FPA-008, JNJ-27301937, JNJ-40346527, PLX-5622, CT-1578, PD-360324, JNJ-28312141; CXC10 chemokine ligand inhibitors, such as 946414-98-8, BMS-936557; CXCR4 chemokine antagonists, such as plerixafor; Cyclin-dependent kinase inhibitor 1 inhibitors, such as CDK-1/2/5/7/9 inhibitors (cancer/tumorogenesis/rheumatoid arthritis), BioPatterns; Cyclin-dependent kinase-2 inhibitors, such as seliciclib, BP-14; Cyclin-dependent kinase-4 inhibitors, such as CDK-4/6 inhibitor (rheumatoid arthritis), Teijin; Cyclin-dependent kinase-5 inhibitors, such as BP-14; Cyclin-dependent kinase-6 inhibitors, such as CDK-4/6 inhibitor (rheumatoid arthritis), Teijin; Cyclin-dependent kinase-7 inhibitors, such as BP-14, seliciclib; Cyclin-dependent kinase-9 inhibitors, such as BP-14, seliciclib; Cyclooxygenase 2 inhibitors, such as celecoxib, etoricoxib, polmacoxib, laflunimus, etodolac, meloxicam, IB-RA (injectable, rheumatoid arthritis), Innobioscience, IB-RA (oral, rheumatoid arthritis), Innobioscience, SKLB-023, meloxicam, lumiracoxib; Cyclooxygenase 2 modulators, such as DRGT-46; Cyclooxygenase inhibitors, such as aceclofenac, diclofenac, imidazole salicylate, naproxcinod, naproxen etemesil, misoprostol with diclofenac, nabumetone, naproxen with esomeprazole, naproxen with esomeprazole strontium, once-daily naproxen (oral controlled release, pain), Alvogen, pelubiprofen, LY-210073, tenoxicam, licofelone, NS-398, bromfenac, L-746483, LY-255283, tenidap, tepoxalin, flobufen, ibuprofen, flurbiprofen, SKF-86002, SC-57666, WY-28342, CI-986, bermoprofen; Cytosolic phospholipase A2 inhibitors, such as AVX-002; Cytotoxic T-lymphocyte protein-4 modulators, such as belatacept, ES-210; Cytotoxic T-lymphocyte protein-4 stimulators, such as abatacept, abatacept biosimilar, BMS-188667; DHFR inhibitors, such as methotrexate, MPI-2505, MBP-Y003; Diamine acetyltransferase inhibitors, such as diminazene aceturate; Dihydroorotate dehydrogenase inhibitors, such as DHODH inhibitors (rheumatoid arthritis/autoimmune diseases), East China University of Science and Technology, ASLAN-003, laflunimus, leflunomide, HWA-486, ABR-224050; Elongation factor 2 inhibitors, such as denileukin diftitox; Eotaxin 2 ligand inhibitors, such as CM-102; EP4 prostanoid receptor antagonists, such as CR-6086; Erythropoietin receptor agonists, such as cibinetide; Fas ligands, such as AP-300; FGF-2 ligand inhibitors, such as RBM-007; FK506 binding protein-12 modulators, such as temsirolimus; Folate antagonists, such as methotrexate, MBP-Y003; Folate receptor agonists, such as folate receptor modulators (chimeric protein, cancer/rheumatoid arthritis), Proda Biotech; Folate receptor modulators, such as technetium (99mTc) etarfolatide; Fractalkine ligand inhibitors, such as E-6011; Fyn tyrosine kinase inhibitors, such as masitinib, laflunimus; G protein coupled receptor 15 antagonists, such as GPR15 antagonists (rheumatoid arthritis/HIV-mediated enteropathy), Omeros; GABA A receptor modulators, such as laflunimus; Glucocorticoid agonists, such as prednisolone, fosdagrocorat; Glucocorticoid antagonists, such as REC-200; Glucocorticoid induced leucine zipper stimulators, such as ART-G01; GM-CSF ligand inhibitors, such as namilumab, MORAb-022, lenzilumab; GM-CSF receptor antagonists, such as mavrilimumab; GM-CSF receptor modulators, such as GSK-3196165; Growth regulated protein alpha ligand inhibitors, such as T-5224; Hwith Kwith ATPase inhibitors, such as naproxen with esomeprazole, naproxen with esomeprazole strontium, ketoprofen with omeprazole, KEO-25001, HC-1004, PN-40020; Histamine H4 receptor antagonists, such as toreforant, GD-48; Histone deacetylase inhibitors, such as givinostat, CHR-5154; Histone deacetylase-6 inhibitors, such as CKD-506; HIV-1 gp120 protein inhibitors, such as maraviroc; HLA class II antigen DQ-2 alpha modulators, such as NexVax2; HLA class II antigen inhibitors, such as HLA-DR1/DR4 inhibitors (rheumatoid arthritis), Provid; HLA class II antigen modulators, such as ARG-301, recombinant T-cell receptor ligand (rheumatoid arthritis), Artielle; Hsp 70 family inhibitors, such as gusperimus trihydrochloride; Hypoxia inducible factor-1 inhibitors, such as 2-methoxyestradiol; IFNB gene stimulators, such as ART-102; I-kappa B kinase beta inhibitors, such as IMD-2560, IMD-0560; I-kappa B kinase inhibitors, such as bardoxolone methyl; IL-1 antagonists, such as rilonacept, IBPB-007-IL, antisense oligonucleotides (rheumatoid arthritis), Leiden University Medical Center, recombinant human interleukin-1 receptor antagonist (rheumatoid arthritis), Shanghai Fudan-Zhangjiang Bio-Pharmaceutical; IL-10 agonists, such as peg-ilodecakin; IL-11 agonists, such as oprelvekin; IL-12 antagonists, such as ustekinumab, briakinumab, ddRNAi therapy (rheumatoid arthritis), Medistem/Benitec; IL-15 antagonists, such as AMG-714, BNZ-132-2; IL-17 antagonists, such as ixekizumab, secukinumab, KD-025; IL-17 receptor modulators, such as CNTO-6785; IL-2 agonists, such as interleukin-2 follow-on biologic; IL-2 antagonists, such as IB-RA (injectable, rheumatoid arthritis), Innobioscience, IB-RA (oral, rheumatoid arthritis), Innobioscience, BNZ-132-2; IL-21 antagonists, such as NN-8828, BNZ-132-2; IL-23 antagonists, such as ustekinumab, briakinumab; IL-3 antagonists, such as anti-IL-3 mAbs (rheumatoid arthritis), University of Regensburg; IL-4 agonists, such as SER-130-AMI; IL-6 antagonists, such as olokizumab, clazakizumab, sirukumab, SA-237, tocilizumab, ALX-0061, FB-704A, OP-R003, peptide IL-6 antagonist, MEDI-5117, T-5224, humanized anti-IL-6 mAb, tocilizumab biosimilar, IL-6 neutralizing human antibodies, anti-IL6 antibody, RN-486, BLX-1002, AMG-220, FM-101, K-832, BLX-1025, esonarimod, TA-383; IL-6 receptor modulators, such as tocilizumab, tocilizumab biosimilar, RO-4877533; Immunoglobulin antagonists, such as iguratimod; Immunoglobulin G1 agonists, such as canakinumab, infliximab biobetter, infliximab biosimilar, BX-2922, STI-002, HF-1020; Immunoglobulin G1 antagonists, such as YHB-1411-2; Immunoglobulin G1 modulators, such as CFZ-533, lenzilumab; Immunoglobulin G2 antagonists, such as denosumab; Immunoglobulin G2 modulators, such as PF-547659; Immunoglobulin gamma Fc receptor II modulators, such as MGD-010; Immunoglobulin gamma Fc receptor IIB antagonists, such as XmAb-5871; Immunoglobulin kappa modulators, such as lenzilumab; Immunoglobulin M antagonists, such as IB-RA (injectable, rheumatoid arthritis), Innobioscience, IB-RA (oral, rheumatoid arthritis), Innobioscience; Inducible nitric oxide synthase inhibitors, such as SKLB-023; Inosine monophosphate dehydrogenase inhibitors, such as mycophenolate mofetil; Insulin sensitizers, such as rosiglitazone, THR-0921, HE-3286, BLX-1002; Integrin alpha-1/beta-1 antagonists, such as SAN-300; Integrin alpha-4/beta-1 antagonists, such as natalizumab; Integrin antagonists, such as PEG-HM-3, CY-9652; Interferon beta ligands, such as recombinant interferon beta-la, TA-383; Interferon gamma ligands, such as interferon gamma follow-on biologic; Interleukin 17A ligand inhibitors, such as ABT-122, bimekizumab, ABBV-257; Interleukin 17F ligand inhibitors, such as bimekizumab; Interleukin 23A inhibitors, such as guselkumab; Interleukin ligands, such as IBPB-007-IL; Interleukin receptor 17A antagonists, such as brodalumab; Interleukin-1 beta ligand inhibitors, such as canakinumab, rilonacept, T-5224, gevokizumab, BLX-1002, LY-2189102, PMI-001, K-832, CDP-484; Interleukin-10 ligands, such as PF-06687234; Interleukin-2 ligands, such as denileukin diftitox, recombinant interleukin-2, interleukin-2 follow-on biologic, recombinant human interleukin-2, interleukin-2 (injectable); Interleukin-4 ligands, such as Tetravil; Interleukin-6 ligand inhibitors, such as gerilimzumab, PF-4236921; Itk tyrosine kinase inhibitors, such as ARN-4079; JAK tyrosine kinase inhibitors, such as tofacitinib, SHR-0302, cerdulatinib, peficitinib, deuterated tofacitinib analog, SD-900, CVXL-0074; Jak1 tyrosine kinase inhibitors, such as ABT-494, baricitinib, ruxolitinib, filgotinib, tofacitinib, itacitinib, peficitinib, NIP-585, CS-944X, YJC-50018, GLPG-0555, MRK-12; Jak2 tyrosine kinase inhibitors, such as baricitinib, ruxolitinib, CT-1578; JAK3 gene inhibitors, such as GBL-5b; Jak3 tyrosine kinase inhibitors, such as decernotinib, tofacitinib, peficitinib, AC-0025, CS-944X, DNX-04042, MTF-003, ARN-4079, PS-020613; Jun N terminal kinase inhibitors, such as IQ-1S; KCNA voltage-gated potassium channel-3 modulators, such as MRAD-P1; Kelch like ECH associated protein 1 modulators, such as dimethyl fumarate; Kit tyrosine kinase inhibitors, such as imatinib, masitinib; LanC like protein 2 modulators, such as BT-11; LITAF gene inhibitors, such as GBL-5b; Lymphocyte function antigen-3 receptor antagonists, such as alefacept; Lyn tyrosine kinase inhibitors, such as masitinib; Macrophage mannose receptor 1 modulators, such as technetium Tc 99m tilmanocept; MAdCAM inhibitors, such as PF-547659; MAP kinase modulators, such as SKLB-023; MAP3K2 gene inhibitors, such as GBL-5b; MAPKAPK5 inhibitors, such as GLPG-0259; Matrix metalloprotease inhibitors, such as GLPG-0259; MCL1 gene inhibitors, such as seliciclib; MEK protein kinase inhibitors, such as binimetinib, AD-GL0001; MEK-1 protein kinase inhibitors, such as binimetinib; MEK-2 protein kinase inhibitors, such as binimetinib; Membrane copper amine oxidase inhibitors, such as BTT-1023, PRX-167700, vepalimomab; Metalloprotease-2 inhibitors, such as ERG-240; Metalloprotease-9 inhibitors, such as GS-5745, ERG-240; Midkine ligand inhibitors, such as CAB-102; Mitochondrial 10 kDa heat shock protein stimulators, such as INV-103; mTOR complex 1 inhibitors, such as everolimus; mTOR inhibitors, such as everolimus, temsirolimus; NAD ADP ribosyltransferase stimulators, such as denileukin diftitox; NAMPT gene inhibitors, such as ART-D01; NF kappa B inhibitor stimulators, such as denosumab; NFAT gene inhibitors, such as T-5224; NFE2L2 gene stimulators, such as bardoxolone methyl; Nicotinic acetylcholine receptor antagonists, such as RPI-78, RPI-MN; NK cell receptor modulators, such as masitinib; NKG2 A B activating NK receptor antagonists, such as monalizumab; NKG2 D activating NK receptor antagonists, such as NNC-0142-002; Nuclear erythroid 2-related factor 2 stimulators, such as dimethyl fumarate; Nuclear factor kappa B inhibitors, such as bardoxolone methyl, IB-RA (injectable, rheumatoid arthritis), Innobioscience, dehydroxymethylepoxyquinomicin, HE-3286, IMD-0560, MP-42, tarenflurbil, VGX-1027, SKLB-023, SP-650003, MG-132, SIM-916, VGX-350, VGX-300, GIT-027, SP-100030, MLN-1145, NVP-IKK-005; Nuclear factor kappa B modulators, such as REM-1086; Nuclear factor kappa B p105 inhibitors, such as REM-1086; Opioid growth factor receptor agonists, such as metenkefalin acetate with tridecactide acetate, FAR-404; Opioid receptor delta antagonists, such as HS-378; Osteoclast differentiation factor antagonists, such as denosumab, cyclic peptidomimetics (rheumatoid arthritis/osteoporosis), University of Michigan; Osteoclast differentiation factor ligand inhibitors, such as denosumab; Oxidoreductase inhibitors, such as etodolac, imidazole salicylate; P2X7 purinoceptor agonists, such as givinostat; p38 MAP kinase alpha inhibitors, such as VX-745, BMS-582949 prodrugs, BMS-751324; p38 MAP kinase inhibitors, such as BCT-197, losmapimod, ARRY-797; PDE 4 inhibitors, such as apremilast; PDE 5 inhibitors, such as PDE5 inhibitors (rheumatoid arthritis), University of Rochester; PDGF receptor agonists, such as oprelvekin; PDGF receptor antagonists, such as imatinib, masitinib; PDGF-B ligand inhibitors, such as SL-1026; PERK gene inhibitors, such as binimetinib; Phosphoinositide-3 kinase delta inhibitors, such as duvelisib, RP-6503, CT-732, INK-007, GNE-293; Phosphoinositide-3 kinase gamma inhibitors, such as duvelisib, RP-6503; Phospholipase A2 inhibitors, such as AVX-002, human secreted phospholipase A2 type IIA-integrin binding inhibiting peptides (rheumatoid arthritis/asthma/Alzheimer's disease/cancer), University of California, Davis, AK-106, varespladib methyl, Ro-31-4493, BM-162353, Ro-23-9358, YM-26734; Platelet activating factor receptor antagonists, such as piperidone hydrochloridum; PPAR gamma agonists, such as rosiglitazone, THR-0921, rosiglitazone XR, etalocib; Programmed cell death protein 1 modulators, such as INSIX RA; Prostaglandin D synthase stimulators, such as HF-0220; Protein arginine deiminase inhibitors, such as PAD inhibitors (rheumatoid arthritis), Leiden University Medical Center/LURIS; Protein tyrosine kinase inhibitors, such as leflunomide; PurH purine biosynthesis protein inhibitors, such as mycophenolate mofetil; Rho associated protein kinase 2 inhibitors, such as KD-025; Seprase inhibitors, such as anti-fibroblast-activation protein (FAP) antibody radiotracers (rheumatoid arthritis), Hoffmann-La Roche/Radboud University; Signal transducer CD24 modulators, such as CD24-IgFc; Signal transduction inhibitors, such as imatinib; Sodium glucose transporter-2 inhibitors, such as THR-0921; Sphingosine 1 phosphate phosphatase modulators, such as S1p modulators (oral, multiple sclerosis/ulcerative colitis/rheumatoid arthritis), Akaal Pharma; STAT3 gene inhibitors, such as bardoxolone methyl, vidofludimus; Superoxide dismutase stimulators, such as imisopasem manganese; SYK family tyrosine kinase inhibitors, such as MK-8457; Syk tyrosine kinase inhibitors, such as fostamatinib, entospletinib, KDDF-201110-06, HMPL-523, cerdulatinib, AB-8779, GS-9876, PRT-2607, CVXL-0074, CG-103065 and CG-026806; Syndecan-1 inhibitors, such as indatuximab ravtansine; T cell receptor antagonists, such as TCR inhibiting SCHOOL peptides (systemic/topical, rheumatoid arthritis/dermatitis/scleroderma), SignaBlok, CII modified peptide (rheumatoid arthritis), Peking University; T cell receptor modulators, such as ARG-301; T cell surface glycoprotein CD28 inhibitors, such as abatacept, belatacept, abatacept biosimilar, RhuDex, BMS-188667; T cell surface glycoprotein CD28 stimulators, such as TAB-08; TAK1 binding protein modulators, such as epigallocatechin 3-gallate; Talin modulators, such as short-form talin regulators (rheumatoid arthritis), KayteeBio; T-cell differentiation antigen CD6 inhibitors, such as itolizumab; T-cell surface glycoprotein CD8 inhibitors, such as tregalizumab; Tenascin modulators, such as Tetravil; TGF beta agonists, such as tregalizumab; Thymulin agonists, such as Syn-1002; TLR-2 antagonists, such as VB-201, P-13; TLR-4 antagonists, such as VB-201, P-13; TLR-9 antagonists, such as P-13; TNF alpha ligand inhibitors, such as adalimumab biosimilar-YHB-1411-2, adalimumab, infliximab, infliximab biosimilar, recombinant humanized anti-TNF-alpha monoclonal antibody, certolizumab pegol, golimumab, ozoralizumab, AT-132, etanercept biosimilar, ISIS-104838, ISU-202, CT-P17, MB-612, Debio-0512, anti-TNF alpha human monoclonal antibody, infliximab biobetter, UB-721, KN-002, DA-3113, BX-2922, R-TPR-015, BOW-050, PF-06410293, CKD-760, CHS-1420, GS-071, ABP-710, STI-002, BOW-015, FKB-327, BAX-2200, HLX-03, BI-695501, CNTO-148, MYL-1401AABP-501, HOT-3010, BAX-2923, SCH-215596, ABT-D2E7, BAT-1406, XPro-1595, Atsttrin, SSS-07, golimumab biosimilar, TA-101, adalimumab follow-on biologic, BLX-1002, ABX-0401, TAQ-588, golimumab biosimilar, TeHL-1, placulumab, PMI-001, tgAAV-TNFR:Fc, K-832, CYT-007-TNFQb, SSR-150106, PassTNF, Verigen, DOM-0200, DOM-0215, AME-527, anti-TNF-alpha mAb, GENZ-38167, BLX-1028, CYT-020-TNFQb, CC-1080, CC-1069; TNF alpha ligand modulators, such as MM-A01-01, CDP-571, camobucol; TNF antagonists, such as etanercept, certolizumab pegol, etanercept follow-on biologic, etanercept biosimilar, DNX-114, TNF antagonist with IL-12 antagonist (rheumatoid arthritis), University of Oxford, BN-006, SCB-131, pegsunercept, GBL-5b, ACE-772, onercept, DE-096, PN-0615, lenercept, ITF-1779, MDL-201112, BAX-2200, SCB-808, DA-3853, HD-203; TNF gene inhibitors, such as GIBH-R-001-2; TNF receptor modulators, such as recombinant TNF receptor 2-Fc fusion protein mutant, T-0001, tgAAV-TNFR:Fc; TNFSF11 gene inhibitors, such as denosumab; Transcription factor p65 inhibitors, such as REM-1086; Transcription factor RelB inhibitors, such as REM-1086; Transferrin modulators, such as methotrexate, MBP-Y003; Tumor necrosis factor 13C receptor antagonists, such as VAY-736; Tumor necrosis factor 15 ligand inhibitors, such as anti-TL1A antibodies (rheumatoid arthritis/inflammatory bowel disease), NIAMS; Tumor necrosis factor ligand 13 inhibitors, such as atacicept; Tumor necrosis factor ligand inhibitors, such as ABBV-257, etanercept biosimilar, ABT-122; Type I IL-1 receptor antagonists, such as anakinra, anakinra biosimilar, anakinra follow-on biologic, AXXO; Type I TNF receptor antagonists, such as NM-9405; Type II TNF receptor modulators, such as etanercept, SCB-131, etanercept biosimilar, etanercept follow-on biologic, BAX-2200, SCB-808, LBEC-0101, DMB-3853, DWP-422, BT-D001, DA-3853; Unspecified GPCR agonists, such as NCP-70X; VEGF receptor antagonists, such as 2-methoxyestradiol and NSC-650853, SL-1026; VEGF-2 receptor antagonists, such as CG-026806; VEGF-2 receptor modulators, such as VEGFR2 neutralizing antibody (rheumatoid arthritis), University of Rochester; VEGF-B ligand inhibitors, such as CSL-346; X-linked inhibitor of apoptosis protein inhibitors, such as IAP inhibitors (oral), Pharmascience; and Zap70 tyrosine kinase inhibitors, such as MK-8457, CT-5332.

Combinations for Metabolic Diseases or Conditions

Examples of metabolic disorders include, without limitation, diabetes, including type I and type II diabetes, metabolic syndrome, dyslipidemia, obesity, glucose intolerance, hypertension, elevated serum cholesterol, and elevated triglycerides. Examples of therapeutic agents used to treat metabolic disorders include antihypertensive agents and lipid lowering agents. Additional therapeutic agents used to treat metabolic disorders include insulin, sulfonylureas peroxisome proliferator activated receptor gamma (PPAR-γ) agonists, such as thiazolidinediones such as Pioglitazones, biguanides, alpha-glucosidase inhibitors, Vitamin E and incretin mimetics. Thus, one aspect of the disclosure is a method of treating a metabolic disease comprising administering a compound of the disclosure in combination with one or more compounds useful for the treatment of metabolic diseases to a subject, particularly a human subject, in need thereof.

Pharmaceutical Compositions

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, or a pharmaceutically acceptable salt thereof. In some embodiments, the pharmaceutical compositions described herein contain not more than about 400 mg of the compound of Formula I. In some embodiments, the pharmaceutical compositions described herein contain about 100 mg of the compound of Formula I, or a pharmaceutically acceptable salt thereof.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of Formula I (herein referred to as the active ingredients), or a pharmaceutically acceptable salt thereof, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Formulation Example 2

A tablet Formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Formulation Example 5

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 6

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation Example 7

A subcutaneous formulation may be prepared as follows:

| Ingredient | Quantity |
| --- | --- |
| Active Ingredient | 5.0 mg |
| Corn Oil | 1.0 mL |

Formulation Example 8

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Formulation Example 9

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Formulation Example 10

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

Sustained release formulations of this disclosure may be prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers-Eudragit® E-Rohm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e., the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Formulation Example 11

A tablet Formula Is prepared using the ingredients below:

| Ingredient | Quantity (mg/tablet) |
| --- | --- |
| Active Ingredient | 300.0 |
| Cellulose, microcrystalline | 100.0 |
| Colloidal silicon dioxide | 10.0 |
| Stearic acid | 5.0 |

The components are blended and compressed to form tablets.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
| --- | --- |
| °C. | Degree Celsius |
| Ac | Acetyl |
| aq. | Aqueous |
| ATP | Adenosine triphosphate |
| $B_2Pin_2$ | Bis(pinacolato)diboron |
| BOC | tert-Butoxycarbonyl |
| Br | Broad |
| BSA | Bovine serum albumin |
| d | Doublet |
| DCM | Dichloromethane |
| dd | Doublet of doublets |
| ddd | Doublet of doublet of doublets |
| DIPEA | N,N-Diisopropylethylamine (Hunig's Base) |
| DMA | Dimethylacetamide |
| DME | 1,2-Dimethoxyethane |
| DMF | Dimethylformamide |
| DMSO | Dimethylsulfoxide |
| dt | Doublet-triplet |
| DTT | Dithiothreitol (Cleland's reagent) |
| $EC_{50}$ | The half maximal effective concentration |
| EDC | 1-(3-dimethylaminopropyl)-3-ethylcarbodiimide |
| EDTA | Ethylenediaminetetraacetic acid |
| EGFR | Epidermal growth factor receptor |
| Eq | Equivalents |
| ES/MS | Electrospray mass spectrometry |
| Et | Ethyl |
| EtOAc | Ethyl acetate |
| EtOH | Ethanol (Ethyl alcohol) |
| FBS | Fetal bovine serum |
| g | Grams |
| HATU | 1-[Bis(dimethylamino)methylene]-1H-1,2,3-triazolo[4,5-b]pyridinium 3-oxid hexafluorophosphate |
| HEPES | 2-[4-(2-hydroxyethyl)piperazin-1-yl]ethanesulfonic acid |
| HCl | Hydrochloric acid |
| HPLC | High pressure liquid chromatography |
| Hrs | Hours |
| HTRF ® | Homogeneous time resolved fluorescence, a registered trademark of Cisbio Bioassays, parc marcel boiteux 30200 codolet, France |
| Hz | Hertz |
| IBD | Inflammatory bowel disease |
| $IC_{50}$ | Half-maximal inhibitory concentration |
| i-pr | Isopropyl |
| J | Coupling constant (MHz) |
| $K_3PO_4$ | Tripotasium phosphate |
| KOtBu | Potassium tert-butoxide |
| KOAc | Potassium Acetate |
| LCMS | Liquid chromatography-mass spectrometry |
| Li HMDS | Lithium bis(trimethylsilyl)amide |
| LiOH | Lithium hydroxide |
| LiI | Lithium iodide |
| LPS | Lipopolysaccharide |
| M | Molar |
| m | multiplet |

| Abbreviation | Meaning |
|---|---|
| M+ | Mass peak |
| M + H+ | Mass peak plus hydrogen |
| Me | Methyl |
| MeCN | Acetonitrile |
| MeOH | Methanol (Methyl alcohol) |
| MeLi | Methyllithium |
| MeMgX | Methylmagnesium halide (Grignard reagent), where X is Fluoro, Chloro, Bromo or Iodo |
| $Me_6Sn_2$ | Hexamethyldistannane (hexamethylditin) |
| mg | Milligram |
| $MgSO_4$ | Magnesium sulfate |
| MHz | Megahertz |
| Min | Minute |
| ml/mL | Milliliter |
| mM | Millimolar |
| mmol | Millimole |
| MS | Mass spectroscopy |
| MsCl | Mesyl chloride |
| NBS | N-Bromosuccinimide |
| n- | Normal |
| nBu/Bu | n-Butyl (normal Butyl) |
| n-BuLi | n-Butyl Lithium |
| NaH | Sodium hydride |
| $NaHCO_3$ | Sodium bicarbonate |
| $NaN_3$ | Sodium azide |
| $Na_3PO_4$ | Trisodium phosphate |
| $Na_2SO_4$ | Sodium sulfate |
| nL | Nanoliter |
| nm | Nanometer |
| NMP | 1-methylpyrrolidin-2-one |
| NMR | Nuclear magnetic resonance |
| NP-40 | Nonyl phenoxypolyethoxylethanol |
| Pd-PEPPSI™-IPent | [1,3-bis(2,6-di-3-pentylphenyl)imidazol-2-ylidene](3-chloropyridyl)palladium(II) dichloride |
| Pen-Strep | Penicillin-Streptomycin (5,000 units of penicillin G sodium salt, and 5,000 µg streptomycin sulfate in 0.85% saline) |
| Ph | Phenyl |
| q | Quartet |
| q.s. | Quantity sufficient to achieve a stated function |
| RP | Reverse phase |
| RPMI | Roswell Park Memorial Institute medium |
| Rt | Room temperature |
| s | Singlet |
| sat. | Saturated |
| Selectfluor® | 1-Chloromethyl-4-fluoro-1,4-diazoniabicyclo[2.2.2]octane bis (a trademark of Air Products and Chemicals) |
| SFC | Supercritical fluid chromatography |
| SiliaMetS® Thiol | Silica-based Palladium scavenger, registered trademark of Silicycle |
| T | Triplet |
| THF | Tetrahydrofuran |
| TFA | Trifluoroacetic acid |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |

1. Comparative Example A

Comparative Example A is shown as Example 193 in International Patent Application PCT/US2016/038861, published as WO 2016/210036 A1. The structure of Comparative Example A is:

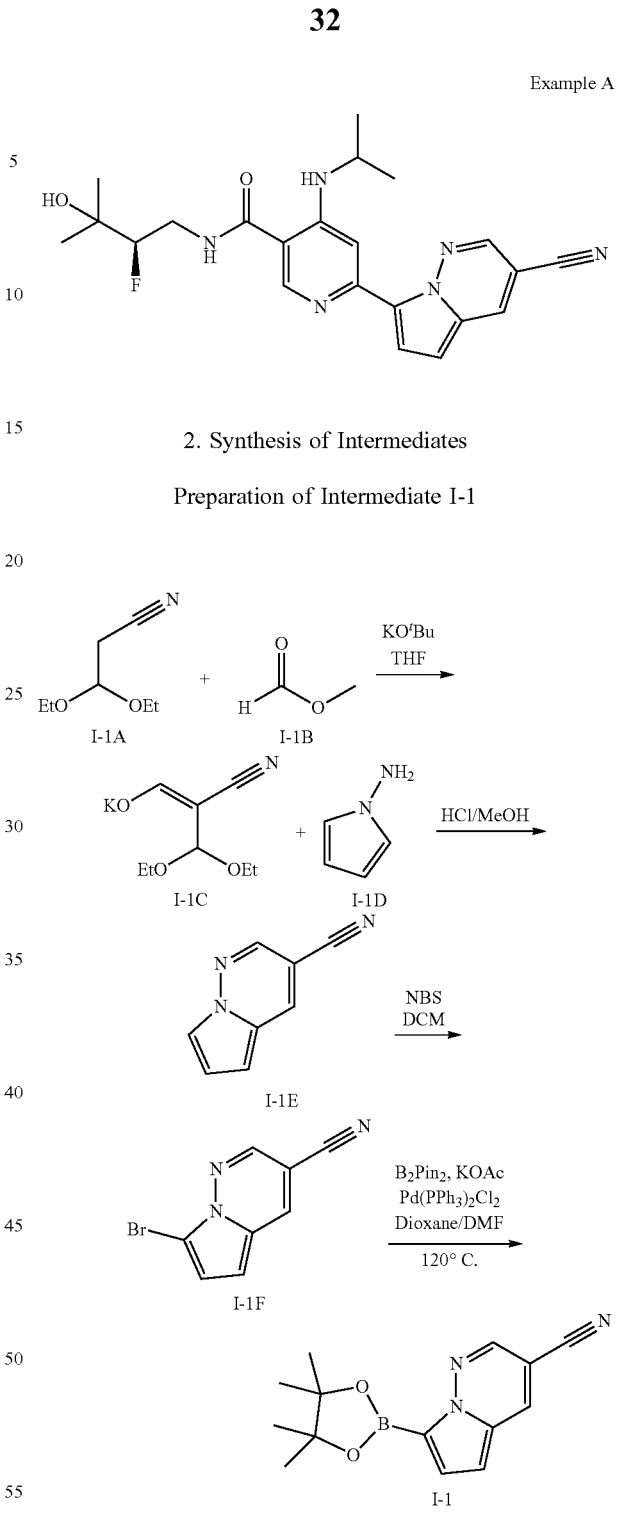

Example A

2. Synthesis of Intermediates

Preparation of Intermediate I-1

3,3-Diethoxy-2-formylpropionitrile Potassium Salt (I-1C)

To a stirred solution of 3,3-diethoxypropane-nitrile (I-1A, 283.80 g, 1.98 moles) and methyl formate (I-1B, 148.80 g, 2.48 moles) in anhydrous THF (1.1 L) at 10° C. was added 1.0 M potassium tert-butoxide in THF (2.2 L, 2.2 moles). The temperature was maintained in the range of 10° C. to 15° C. throughout the 4.5 minute addition. Following the addition, the resulting slurry was stirred for 2 hours at ambient temperature. Hexane (400 mL) was then added and stirring was continued for another 20 min. The slurry was filtered and the cake washed with 1/1 hexanes/THF and dried overnight at 60° C. in a vacuum oven to provide I-1C, $^1$H-NMR (CD$_3$OD) was consistent with the desired structure.

Pyrrolo[1,2-b]pyridazine-3-carbonitrile (I-1E)

A stirred suspension of 3,3-diethoxy-2-formylpropionitrile potassium salt (I-1C, 5.10 g, 24.36 mmol) was cooled to 0° C., and concentrated HCl (7.11 mL, 85.26 mmol) was added dropwise at such a rate that the internal temperature of the reaction did not go above 20° C. After addition was complete, the reaction was stirred at room temperature for 20 minutes. To this reaction mixture was added a solution of 1-aminopyrrole (I-1D, 1.00 g, 12.18 mmol) in methanol (4.0 mL). After addition, the reaction mixture was refluxed at 90° C. for 2 hours. When heating was complete, the reaction was cooled to room temperature and concentrated to about half of the original volume. Saturated aqueous sodium bicarbonate was added carefully to the resulting residue until bubbling stopped. The solution was extracted with two portions of ethyl acetate. The combined organic layers were dried over sodium sulfate, filtered, concentrated in vacuo, and the resulting residue was purified by silica gel chromatography (eluent: EtOAc/hexanes) to provide I-1E.

1H NMR (400 MHz, Chloroform-d) δ 8.16-8.03 (m, 2H), 7.93 (ddd, J=2.6, 1.4, 0.6 Hz, 1H), 7.04 (dd, J=4.5, 2.7 Hz, 1H), 6.84 (dd, J=4.6, 1.4 Hz, 1H).

7-bromopyrrolo[1,2-b]pyridazine-3-carbonitrile (I-1F)

To a solution of pyrrolo[1,2-b]pyridazine-3-carbonitrile (I-1E, 840.0 mg, 5.9 mmol) in MeCN (30 mL) at room temperature was added N-bromosuccinimide in one portion. The reaction was stirred at room temperature for 30 minutes then poured into saturated aqueous sodium bicarbonate. The solution was concentrated in vacuo to remove the acetonitrile. The resulting aqueous layer was extracted with three portions of EtOAc. The combined organic layers were dried over sodium sulfate, filtered, concentrated in vacuo, and purified by silica gel chromatography (eluent: EtOAc/hexanes) to provide I-1F.

1H NMR (400 MHz, Chloroform-d) δ 8.28 (d, J=2.1 Hz, 1H), 8.10 (d, J=2.1 Hz, 1H), 7.12 (d, J=4.8 Hz, 1H), 6.93 (d, J=4.8 Hz, 1H).

7-(4,4,5,5-tetramethyl-1,3,2-dioxaborolan-2-yl)pyrrolo[1,2-b]pyridazine-3-carbonitrile (I-1)

A microwave vial was charged with 7-bromopyrrolo[1,2-b]pyridazine-3-carbonitrile (I-1F, 416.5 mg, 1.9 mmol), bis(pinacolato)diboron (762.1 mg, 3.0 mmol), potassium acetate (552.3 mg, 5.6 mmol), and bis(triphenylphosphine)palladium(II) dichloride (65.8 mg, 0.094 mmol). Dioxane (8.0 mL) and DMF (4.0 mL) were added, and the reaction mixture was degassed with bubbling argon for 2 minutes. The vial was sealed and the reaction was heated at 120° C. in a microwave reactor for 60 minutes. After cooling, the reaction mixture was filtered and concentrated in vacuo. The resulting residue was partitioned between EtOAc and water. The aqueous layer was extracted with a second portion of EtOAc, and the combined organic layers were dried over sodium sulfate, filtered through a plug of Celite, and concentrated in vacuo. The resulting residue was purified by silica gel chromatography (eluent: EtOAc/hexanes) to provide I-1.

1H NMR (400 MHz, Chloroform-d) δ 8.31 (d, J=2.3 Hz, 1H), 8.14 (d, J=2.2 Hz, 1H), 7.52 (d, J=4.6 Hz, 1H), 6.84 (d, J=4.6 Hz, 1H), 1.41 (s, 12H).

Preparation of Intermediate I-2

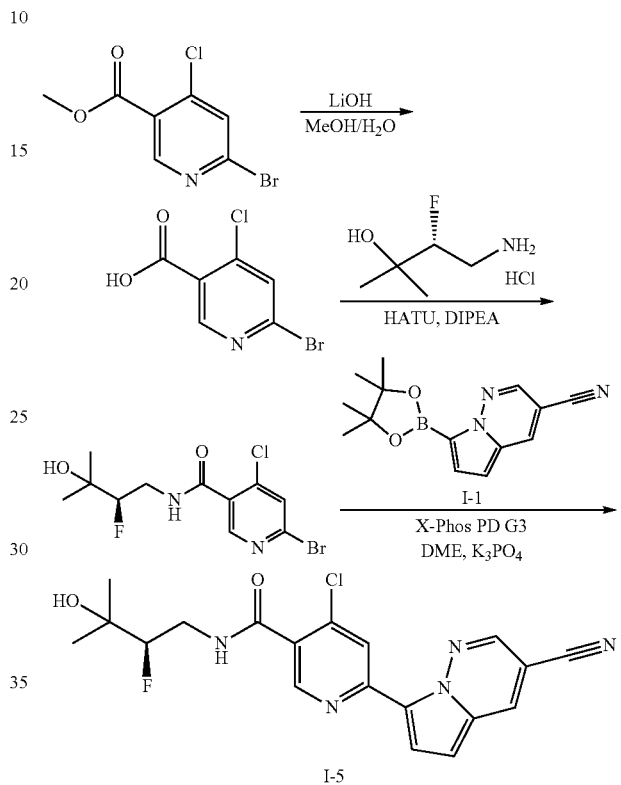

6-bromo-4-chloronicotinic acid. To a solution of methyl 6-bromo-4-chloronicotinate (15 g, 59.89 mmol) in methanol (240 mL) was added lithium hydroxide (2.93 g, 119.77 mmol) in water (68 mL). The solution was heated to 43° C. overnight and subsequently cooled to room temperature. Aqueous hydrochloric acid (1M, 120 mL) was added and volatiles were removed in vacuo. The resulting slurry was filtered and washed with H$_2$O to provide 6-bromo-4-chloronicotinic acid.

ES/MS: 238.0 (M+H$^+$).

1H NMR (400 MHz, DMSO-d6) δ 8.75 (s, 1H), 8.03 (s, 1H).

(R)-6-bromo-4-chloro-N-(2-fluoro-3-hydroxy-3-methylbutyl)nicotinamide

To a solution of 6-bromo-4-chloronicotinic acid (3 g, 12.69 mmol) in DMF (42 mL) was added HATU (6.27 g, 16.49 mmol), (R)-4-amino-3-fluoro-2-methylbutan-2-ol hydrochloride (2.4 g, 15.23 mmol), and N,N-Diisopropylethylamine (5.62 ml, 32.26 mmol). The resulting solution was stirred at room temperature overnight and subsequently diluted with ethyl acetate. The organic solution was washed with saturated aqueous lithium chloride (3 times), then dried over Na$_2$SO$_4$, and then concentrated. The residue was purified by silica gel chromatography (eluent: EtOAc/hexanes) to provide (R)-6-bromo-4-chloro-N-(2-fluoro-3-hydroxy-3-methylbutyl)nicotinamide.

ES/MS: 341.1 (M+H$^+$).

1H NMR (400 MHz, DMSO-d$_6$) δ 8.88 (t, J=5.5 Hz, 1H), 8.41 (s, 1H), 8.01 (s, 1H), 4.82 (s, 1H), 4.28 (ddd, J=49.3, 9.4, 2.0 Hz, 1H), 3.84-3.63 (m, 1H), 3.40-3.22 (m, 1H), 1.13 (d, J=7.0 Hz, 6H).

(R)-4-chloro-6-(3-cyanopyrrolo[1,2-b]pyridazin-7-yl)-N-(2-fluoro-3-hydroxy-3-methylbutyl)nicotinamide (I-5)

To a solution of (R)-6-bromo-4-chloro-N-(2-fluoro-3-hydroxy-3-methylbutyl)nicotinamide (0.2 g, 0.59 mmol) in DME (3.9 mL) was added 7-(4,4,5,5-tetramethyl-1,3,2-dioxaborolan-2-yl)pyrrolo[1,2-b]pyridazine-3-carbonitrile (0.24 g, 0.9 mmol), XPhos Pd G3 (0.05 g, 0.06 mmol), and aqueous potassium phosphate tribasic (2M, 0.59 mL, 1.18 mmol). The resulting solution was degassed with argon and heated to 120° C. for 12 minutes in a microwave reactor. The crude reaction mixture was purified by silica gel chromatography (eluent: EtOAc/hexanes) to provide (R)-4-chloro-6-(3-cyanopyrrolo[1,2-b]pyridazin-7-yl)-N-(2-fluoro-3-hydroxy-3-methylbutyl)nicotinamide.

ES/MS: 402.2 (M+H$^+$).

3. Example Procedures and Compound Examples

Procedure 1: Example 1

(R)-6-(3-cyanopyrrolo[1,2-b]pyridazin-7-yl)-N-(2-fluoro-3-hydroxy-3-methylbutyl)-4-(methylamino)nicotinamide

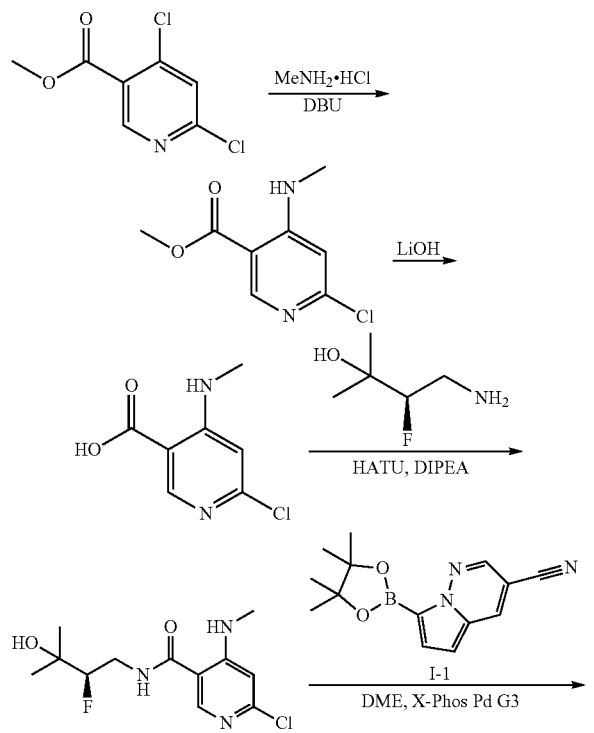

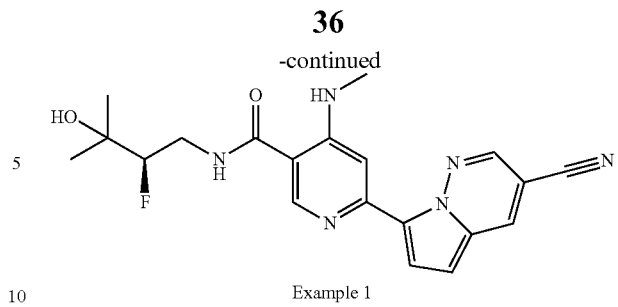

Example 1

Methyl 6-chloro-4-(methylamino)nicotinate

To a solution of methyl 4,6-dichloronicotinate (0.5 g, 2.43 mmol) and methylamine hydrochloride (0.82 g, 12.16 mmol) in acetonitrile (10 mL) and water (0.3 mL) was added 1,8-diazabicyclo(5.4.0)undec-7-ene (1.8 ml, 12.04 mmol). The resulting solution was stirred at room temperature for 3 hours. The solution was concentrated to dryness in vacuo and diluted with ethyl acetate. The resulting solution was washed with water and aqueous sodium chloride. The resulting organic layer was dried over sodium sulfate and concentrated in vacuo. The resulting material was purified normal phase SiO$_2$ chromatography (eluent: ethyl acetate/hexanes) to provide the desired product.

ES/MS: 201.180 (M+H$^+$).

6-Chloro-4-(methylamino)nicotinic acid

To a solution of methyl 6-chloro-4-(methylamino)nicotinate (0.38 g, 1.92 mmol) in MeOH (10 mL), THF (5 mL), and water (5 mL) was added lithium hydroxide (0.12 g, 5.01 mmol). The solution was stirred at room temperature for 18 h, neutralized with HCl (1N, 5 mL), and concetrated to dry in vacuo. The resulting crude material was used in the subsequent step.

ES/MS: 187.070 (M+H$^+$).

(R)-6-Chloro-N-(2-fluoro-3-hydroxy-3-methylbutyl)-4-(methylamino)nicotinamide

To a solution of 6-chloro-4-(methylamino)nicotinic acid (0.36 g, 1.92 mmol) and (R)-4-amino-3-fluoro-2-methylbutan-2-ol (0.31 g, 2.56 mmol) in DMF (10 mL) was added HATU (0.97 g, 2.55 mmol) and N,N-Diisopropylethylamine (1.5 ml, 8.61 mmol). The resulting solution was stirred at room temperature for 1 hour and diluted with ethyl acetate. The solution was washed with 5% aqueous lithium chloride (3×), dried over sodium sulfate, and concentrated in vacuo. The resulting material was purified normal phase SiO$_2$ chromatography (eluent: ethyl acetate/hexanes) to provide the desired product.

ES/MS: 290.472 (M+H$^+$).

(R)-6-(3-cyanopyrrolo[1,2-b]pyridazin-7-yl)-N-(2-fluoro-3-hydroxy-3-methylbutyl)-4-(methylamino)nicotinamide To a solution of (R)-6-chloro-N-(2-fluoro-3-hydroxy-3-methylbutyl)-4-(methylamino)nicotinamide (30 mg, 0.10 mmol), 7-(4,4,5,5-tetramethyl-1,3,2-dioxaborolan-2-yl)pyrrolo[1,2-b]pyridazine-3-carbonitrile (39 mg, 0.15 mmol) and Xphos Pd G3 (9 mg, 0.011 mmol) in DME (1 mL) was added aqueous potasium phosphate (2M, 0.10 mL, 0.20 mmol). The resulting solution was degassed with argon for 2 min and heating under microwave conditions for 20 min at 120° C. The reaction mixture was filtered and the resulting solids were washed with DMF. The filtrates were then concetrated in vacuo and the crude material was purified by RP-HPLC (eluent: water/MeCN*0.1% TFA) to yield the product as a trifluoroacetate salt.

ES/MS: 397.283 (M+H$^+$).

1H NMR (400 MHz, Methanol-d$_4$) δ 8.75 (d, J=2.2 Hz, 1H), 8.66 (d, J=2.2 Hz, 1H), 8.51 (s, 1H), 8.02 (d, J=5.1 Hz, 1H), 7.76 (s, 1H), 7.21 (d, J=5.1 Hz, 1H), 4.42 (ddd, J=49.0, 9.3, 2.1 Hz, 1H), 3.93 (ddd, J=36.4, 14.5, 2.2 Hz, 1H), 3.48 (ddd, J=16.2, 14.5, 9.4 Hz, 1H), 3.19 (s, 3H), 1.28 (d, J=1.7 Hz, 6H).

Procedure 2: Example 2

(R)-4-((cyanomethyl)amino)-6-(3-cyanopyrrolo[1,2-b]pyridazin-7-yl)-N-(2-fluoro-3-hydroxy-3-methyl-butyl)nicotinamide filtered and the solid was washed with EtOAc. The resulting filtrates were combined and washed with aqueous ammonia chloride. The resulting organic layer was dried over magnesium sulfate and concentrated in vacuo. The resulting material was purified normal phase SiO$_2$ chromatography (eluent: ethyl acetate/hexanes) to provide the desired product.

ES/MS: 315.159 (M+H$^+$).

(R)-4-((cyanomethyl)amino)-6-(3-cyanopyrrolo[1,2-b]pyridazin-7-yl)-N-(2-fluoro-3-hydroxy-3-methyl-butyl)nicotinamide To a solution of (R)-6-chloro-4-((cyanomethyl)amino)-N-(2-fluoro-3-hydroxy-3-methylbutyl)nicotinamide (53 mg, 0.17 mmol), 7-(4,4,5,5-tetramethyl-1,3,2-dioxaborolan-2-yl)pyrrolo[1,2-b]pyridazine-3-carbonitrile (68 mg, 0.25 mmol) and Xphos Pd G3 (16 mg, 0.019 mmol) in DME (2 mL) was added aqueous potasium phosphate (2M, 0.17 mL, 0.34 mmol). The resulting solution was degassed with argon for 2 min and heating under microwave conditions for 20 min at 120° C. The reaction mixture was filtered and the

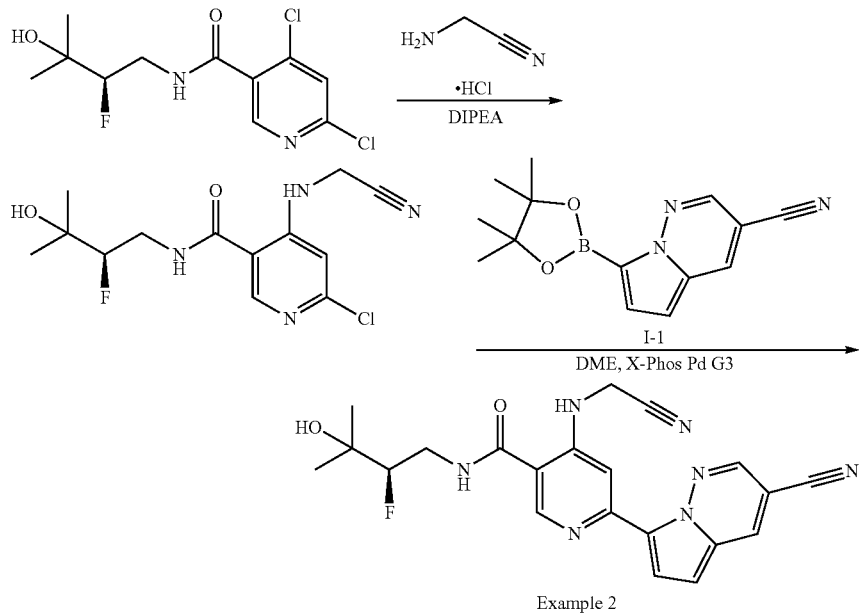

Example 2

(R)-6-chloro-4-((cyanomethyl)amino)-N-(2-fluoro-3-hydroxy-3-methylbutyl)nicotinamide To a slurry of (R)-4,6-dichloro-N-(2-fluoro-3-hydroxy-3-methylbutyl)nicotinamide (100 mg, 0.34 mmol) and aminoacetonitrile hydrochloride (47.03 mg, 0.51 mmol) in DMA (1 mL) was added N,N-diisopropylethylamine (0.2 mL, 1.12 mmol). The resulting solution was then heated under microwave conditions for 30 min at 150° C. Additional aminoacetonitrile hydrochloride (47.03 mg, 0.51 mmol) and N,N-diisopropylethylamine (0.2 mL, 1.12 mmol) were added and the reaction was heated under thermal conditions for 16 hours at 130° C. The solution was cooled to room temperature and diluted with ethyl acetate. The resulting slurry was resulting solids were washed with DMF and MeOH. The filtrates were then concetrated in vacuo and the crude material was purified by RP-HPLC (eluent: water/MeCN*0.1% TFA) to yield the product as a trifluoroacetate salt. The material was further purified by normal phase SiO$_2$ chromatography (eluent: methanol/dichloromethane) and lyophilized from acetonitrile and water (0.1% trifluoroacetic acid) to provide the desired product.

ES/MS: 422.250 (M+H$^+$).

1H NMR (400 MHz, Methanol-d4) δ 8.79 (d, J=2.2 Hz, 1H), 8.70 (d, J=2.0 Hz, 2H), 8.10 (d, J=5.1 Hz, 1H), 8.05 (s, 1H), 7.25 (d, J=5.1 Hz, 1H), 4.73 (s, 2H), 4.46 (ddd, J=49.1, 9.4, 2.2 Hz, 1H), 3.98 (ddd, J=36.6, 14.5, 2.2 Hz, 1H), 3.60-3.41 (m, 1H), 1.31 (d, J=1.7 Hz, 6H).

Procedure 3: Example 3

4-(((R)-1-cyanoethyl)amino)-6-(3-cyanopyrrolo[1,2-b]pyridazin-7-yl)-N—((R)-2-fluoro-3-hydroxy-3-methylbutyl)nicotinamide

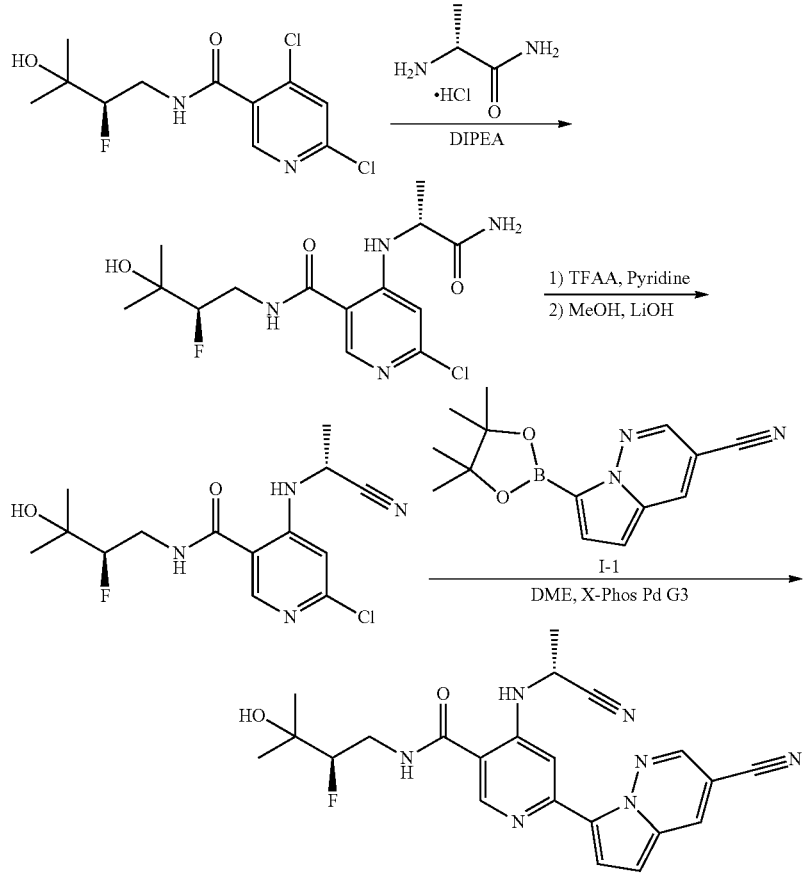

Example 3

4-(((R)-1-amino-1-oxopropan-2-yL)amino)-6-chloro-N—((R)-2-fluoro-3-hydroxy-3-methylbutyl)nicotinamide To a slurry of (R)-4,6-dichloro-N-(2-fluoro-3-hydroxy-3-methylbutyl)nicotinamide (200 mg, 0.68 mmol) and (R)-2-aminopropanamide hydrochloride (172 mg, 1.38 mmol) in DMA (3 mL) was added N,N-diisopropylethylamine (0.6 mL, 3.37 mmol). The resulting solution was then heated under microwave conditions for 60 min at 150° C. The resulting material was purified by RP-HPLC (eluent: water/MeCN*0.1% TFA) to yield the product as a trifluoroacetate salt.

ES/MS: 347.521 (M+H$^+$).

TABLE 1

Compounds

| Compound | ES/MS m/z | Procedure | Name |
|---|---|---|---|
| 1 | 397.3 | 1 | (R)-6-(3-cyanopyrrolo[1,2-b]pyridazin-7-yl)-N-(2-fluoro-3-hydroxy-3-methylbutyl)-4-(methylamino)nicotinamide |
| 2 | 422.3 | 2 | (R)-4-((cyanomethyl)amino)-6-(3-cyanopyrrolo[1,2-b]pyridazin-7-yl)-N-(2-fluoro-3-hydroxy-3-methylbutyl)nicotinamide |
| 3 | 436.4 | 3 | 4-(((R)-1-cyanoethyl)amino)-6-(3-cyanopyrrolo[1,2-b]pyridazin-7-yl)-N-((R)-2-fluoro-3-hydroxy-3-methylbutyl)nicotinamide |
| 4 | 436.3 | 3 | 4-(((S)-1-cyanoethyl)amino)-6-(3-cyanopyrrolo[1,2-b]pyridazin-7-yl)-N-((R)-2-fluoro-3-hydroxy-3-methylbutyl)nicotinamide |

TABLE 1-continued

Compounds

| Compound | ES/MS m/z | Procedure | Name |
|---|---|---|---|
| 5 | 450.4 | 3 | 4-(((R)-1-cyanopropyl)amino)-6-(3-cyanopyrrolo[1,2-b]pyridazin-7-yl)-N-((R)-2-fluoro-3-hydroxy-3-methylbutyl)nicotinamide |
| 6 | 450.3 | 3 | 4-(((S)-1-cyanopropyl)amino)-6-(3-cyanopyrrolo[1,2-b]pyridazin-7-yl)-N-((R)-2-fluoro-3-hydroxy-3-methylbutyl)nicotinamide |
| 7 | 436.5 | 2 | (R)-4-((2-cyanoethyl)amino)-6-(3-cyanopyrrolo[1,2-b]pyridazin-7-yl)-N-(2-fluoro-3-hydroxy-3-methylbutyl)nicotinamide |
| 8 | 450.7 | 2 | (R)-4-((3-cyanopropyl)amino)-6-(3-cyanopyrrolo[1,2-b]pyridazin-7-yl)-N-(2-fluoro-3-hydroxy-3-methylbutyl)nicotinamide |
| 9 | 450.5 | 3 | (R)-4-((2-cyanopropan-2-yl)amino)-6-(3-cyanopyrrolo[1,2-b]pyridazin-7-yl)-N-(2-fluoro-3-hydroxy-3-methylbutyl)nicotinamide |
| 10 | 448.5 | 2 | (R)-4-((1-cyanocyclopropyl)amino)-6-(3-cyanopyrrolo[1,2-b]pyridazin-7-yl)-N-(2-fluoro-3-hydroxy-3-methylbutyl)nicotinamide |

TABLE 2

NMR Data for Exemplified Compounds

| Compound | 1H-NMR |
|---|---|
| 1 | 1H NMR (400 MHz, Methanol-d4) δ 8.75 (d, J = 2.2 Hz, 1H), 8.66 (d, J = 2.2 Hz, 1H), 8.51 (s, 1H), 8.02 (d, J = 5.1 Hz, 1H), 7.76 (s, 1H), 7.21 (d, J = 5.1 Hz, 1H), 4.42 (ddd, J = 49.0, 9.3, 2.1 Hz, 1H), 3.93 (ddd, J = 36.4, 14.5, 2.2 Hz, 1H), 3.48 (ddd, J = 16.2, 14.5, 9.4 Hz, 1H), 3.19 (s, 3H), 1.28 (d, J = 1.7 Hz, 6H) |
| 2 | 1H NMR (400 MHz, Methanol-d4) δ 8.79 (d, J = 2.2 Hz, 1H), 8.70 (d, J = 2.0 Hz, 2H), 8.10 (d, J = 5.1 Hz, 1H), 8.05 (s, 1H), 7.25 (d, J = 5.1 Hz, 1H), 4.73 (s, 2H), 4.46 (ddd, J = 49.1, 9.4, 2.2 Hz, 1H), 3.98 (ddd, J = 36.6, 14.5, 2.2 Hz, 1H), 3.60-3.41 (m, 1H), 1.31 (d, J = 1.7 Hz, 6H). |
| 3 | 1H NMR (400 MHz, Methanol-d4) δ 8.79 (d, J = 2.1 Hz, 1H), 8.73 (s, 1H), 8.71 (d, J = 2.1 Hz, 1H), 8.09 (d, J = 5.1 Hz, 1H), 8.07 (s, 1H), 7.26 (d, J = 5.1 Hz, 1H), 5.15 (q, J = 6.9 Hz, 1H), 4.47 (ddd, J = 49.0, 9.3, 2.1 Hz, 1H), 3.97 (ddd, J = 36.4, 14.6, 2.2 Hz, 1H), 3.54 (ddd, J = 16.2, 14.5, 9.3 Hz, 1H), 1.85 (d, J = 7.0 Hz, 3H), 1.32 (d, J = 1.7 Hz, 6H). |
| 4 | 1H NMR (400 MHz, Methanol-d4) δ 8.79 (d, J = 2.2 Hz, 1H), 8.73 (s, 1H), 8.71 (d, J = 2.2 Hz, 1H), 8.09 (d, J = 5.0 Hz, 1H), 8.07 (s, 1H), 7.26 (d, J = 5.1 Hz, 1H), 5.15 (q, J = 7.0 Hz, 1H), 4.46 (ddd, J = 49.0, 9.4, 2.2 Hz, 1H), 3.99 (ddd, J = 36.3, 14.5, 2.1 Hz, 1H), 3.60-3.43 (m, 1H), 1.85 (d, J = 7.0 Hz, 3H), 1.32 (d, J = 1.7 Hz, 6H). |
| 5 | 1H NMR (400 MHz, Methanol-d4) δ 8.77 (t, J = 1.8 Hz, 1H), 8.73 (d, J = 1.4 Hz, 1H), 8.68 (d, J = 2.0 Hz, 1H), 8.08 (dd, J = 5.2, 1.4 Hz, 1H), 8.04 (d, J = 1.4 Hz, 1H), 7.23 (dd, J = 5.1, 1.4 Hz, 1H), 5.05 (t, J = 6.9 Hz, 1H), 4.45 (ddd, J = 49.0, 9.3, 2.1 Hz, 1H), 3.94 (ddd, J = 36.5, 14.6, 2.3 Hz, 1H), 3.52 (td, J = 15.2, 9.3 Hz, 1H), 2.17 (p, J = 7.2 Hz, 2H), 1.29 (d, J = 1.6 Hz, 6H), 1.25 (td, J = 7.4, 1.4 Hz, 3H). |
| 6 | 1H NMR (400 MHz, Methanol-d4) δ 8.71 (d, J = 2.7 Hz, 1H), 8.63 (d, J = 2.3 Hz, 1H), 8.56 (d, J = 2.3 Hz, 1H), 8.24 (s, 1H), 7.93 (d, J = 4.8 Hz, 1H), 7.13 (d, J = 5.0 Hz, 1H), 4.80 (d, J = 6.3 Hz, 1H), 4.43 (ddd, J = 49.0, 9.2, 2.4 Hz, 1H), 4.09-3.80 (m, 1H), 3.49 (ddd, J = 15.8, 14.3, 9.7 Hz, 1H), 2.14 (p, J = 7.2 Hz, 2H), 1.29 (d, J = 1.8 Hz, 6H), 1.27-1.18 (m, 3H). |
| 7 | 1H NMR (400 MHz, Methanol-d4) δ 8.78 (d, J = 2.1 Hz, 1H), 8.69 (d, J = 2.2 Hz, 1H), 8.63 (s, 1H), 8.09 (d, J = 5.0 Hz, 1H), 7.96 (s, 1H), 7.24 (d, J = 5.1 Hz, 1H), 4.46 (ddd, J = 49.1, 9.4, 2.2 Hz, 1H), 4.10-3.85 (m, 3H), 3.52 (ddd, J = 16.2, 14.5, 9.4 Hz, 1H), 2.97 (t, J = 6.5 Hz, 2H), 1.31 (d, J = 1.7 Hz, 6H). |
| 8 | 1H NMR (400 MHz, Methanol-d4) δ 8.78 (d, J = 2.2 Hz, 1H), 8.70 (d, J = 2.2 Hz, 1H), 8.58 (s, 1H), 8.05 (d, J = 5.1 Hz, 1H), 7.93 (s, 1H), 7.24 (d, J = 5.1 Hz, 1H), 4.45 (ddd, J = 49.0, 9.3, 2.2 Hz, 1H), 3.97 (ddd, J = 36.3, 14.6, 2.2 Hz, 1H), 3.74 (t, J = 7.1 Hz, 2H), 3.51 (ddd, J = 16.2, 14.6, 9.3 Hz, 1H), 2.67 (t, J = 7.0 Hz, 2H), 2.13 (p, J = 7.0 Hz, 2H), 1.31 (d, J = 1.7 Hz, 6H). |
| 9 | 1H NMR (400 MHz, Methanol-d4) δ 8.78 (d, J = 2.2 Hz, 1H), 8.77 (s, 1H), 8.70 (d, J = 2.2 Hz, 1H), 8.57 (s, 1H), 7.99 (d, J = 5.1 Hz, 1H), 7.25 (d, J = 5.1 Hz, 1H), 4.46 (ddd, J = 49.1, 9.4, 2.1 Hz, 1H), 3.96 (ddd, J = 36.5, 14.6, 2.1 Hz, 1H), 3.53 (ddd, J = 16.1, 14.6, 9.4 Hz, 1H), 1.98 (s, 6H), 1.31 (d, J = 1.7 Hz, 6H). |

TABLE 2-continued

NMR Data for Exemplified Compounds

| Compound | 1H-NMR |
|---|---|
| 10 | 1H NMR (400 MHz, Methanol-d4) δ 8.77 (d, J = 2.1 Hz, 1H), 8.73 (d, J = 2.2 Hz, 1H), 8.69 (s, 1H), 8.50 (s, 1H), 8.04 (d, J = 5.1 Hz, 1H), 7.24 (d, J = 5.1 Hz, 1H), 4.43 (ddd, J = 49.0, 9.3, 2.1 Hz, 1H), 3.94 (ddd, J = 36.3, 14.6, 2.1 Hz, 1H), 3.49 (ddd, J = 16.2, 14.6, 9.3 Hz, 1H), 1.97-1.84 (m, 2H), 1.64-1.53 (m, 2H), 1.29 (d, J = 1.6 Hz, 6H). |

Biological Assays

Biological assays were conducted to measure activity against TNFα and IRAK4. As summarized in Table 3, the test compounds are inhibitors of IRAK4.

IRAK4 Monocyte TNFα Cell Based Assay Procedure:

Cryopreserved human monocytes (Stem Cell Technologies) were thawed, diluted in RPMI with GlutaMAX™ (Gibco® 200 mM L-alanyl-L-glutamine) (10 mM HEPES, 1× Pen-Strep, 55 μM B-mercaptoethanol, 1 mM Sodium pyruvate) media containing 10% FBS to 0.125×10⁶ cells/ml and recovered at 37° C. for 2 hours. The cell suspension was then plated at a density of 5,000 cells/well onto black 384 well Greiner clear bottom plates. Plates were pre-spotted with test compounds and serially diluted in DMSO where 40 nL/well were delivered using the Echo 550 acoustic liquid dispenser (Labcyte®) for a final DMSO concentration of 0.1%. Plated cells were treated with compound for 1 hour at 37° C. Cells were then stimulated with 50 pg/ml of LPS (Sigma) excluding outside columns of plate used for unstimulated cell control wells. Cells were incubated for an additional 4 hours at 37° C. Cells were then spun out of the media and 5 μl of sample were taken and analyzed for total TNFα content using the TR-FRET Human TNFα detection system (CisBio). This system utilizes two labeled antibodies (cryptate and XL665) that bind to two different epitopes of the TNFα molecule and produce FRET signal proportional to the concentration of TNFα in the sample. Detection antibodies are mixed 50:50 and 5 μL were dispensed into each well. Plates were covered with clear seals and incubated at room temp overnight. The following morning plates were read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent of control was calculated as follows:

% Control=100×(Ratio$_{Sample}$−Ratio$_{0\% \ stimulation}$)/ (Ratio$_{100\% \ Stimulation}$−Ratio$_{0\% \ Stimulation}$)

where unstimulated cells (0% stimulation) were the negative control and stimulated cells (100% stimulation) were used as the positive control.

IRAK4 Biochemical Assay Procedure:

IRAK4 enzyme (Carna Biosciences, Chuo-ku, Kobe, Japan) activity was measured by detecting phosphorylated peptide substrate formation using an antibody against the phosphorylated peptide substrate. This is a time-resolved fluorescence resonance energy transfer (TR-FRET) immunoassay, based on the STK1 KinEASE Assay (Cisbio, Bedford, Mass.). The assay was designed as a simple two-step, endpoint assay (a 5 μl enzyme reaction followed by 5 μl stop and detect Solution) performed in ProxiPlate-384 Plus plates (Perkin Elmer, Waltham, Mass.). Staurosporine, a non-selective kinase inhibitor was used as a positive control. Compounds diluted in DMSO were spotted into 384 well plates using a Labcyte® Echo 550 Liquid Handling System prior to addition of IRAK4 enzyme and peptide substrate. Reaction solutions were delivered using a Multi-Flo (Bio-Tek Instruments). The enzyme and peptide solution was incubated with compound for 15 minutes at room temp before the reaction was initiated by the addition of ATP. The standard 5 μl reaction mixture contained 500 μM ATP, 2 μM peptide (STK1 Peptide), 0.75 nM of IRAK4 in reaction buffer (50 mM HEPES, pH 7.0, 0.02% NaN₃, 0.01% BSA, 0.1 mM Orthovanadate, 5 mM MgCl₂, 0.025% NP-40, 1 mM DTT). After 120 min of incubation at room temperature, 5 μl of Stop and Detect Solution (1:100 Cryptate labeled anti-phosphorylated peptide antibody solution and 125 nM Tracer in a 50 mM HEPES pH 7.0 detection buffer containing sufficient EDTA) was added. The plate was then further incubated for 60 minutes at room temperature and read on Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percentage of inhibition was calculated as below:

% Inhibition=100×(Ratio$_{Sample}$−Ratio$_{0\% \ Inhibition}$)/ (Ratio$_{100\% \ Inhibition}$−Ratio$_{0\% \ Inhibition}$)

The 0% inhibition value comes from control wells lacking inhibitor. The 100% inhibition value comes from control wells containing a saturating amount of known inhibitor staurosporine.

Hepatic Stability:

Metabolic Stability in Cryopreserved Hepatocytes:

Complete HT medium was prepared by the addition of 1 mL Torpedo Antibiotic Mix to 45 mL of InVitroGRO™ HT medium. Supplemented KHB medium consisted of KrebsHenseleit buffer with amikacin (84 μg/mL), calcium chloride (1 mM), gentamicin (84 μg/mL), HEPES (20 mM), heptanoic acid (4.2 μM) and sodium bicarbonate (28.5 mM) and the pH was adjusted to 7.4 at 37° C. using 1 M NaOH or 1 M HCl. The human cryopreserved hepatocytes were pooled from ten adult donors (Celsis, Lot: HBZ).

Vials containing cryopreserved hepatocytes were removed from liquid nitrogen and immediately immersed in a 37° C. water bath. The vials were shaken gently until the contents had thawed and were then immediately emptied into 48 mL of pre warmed Complete HT Medium in a 50 mL conical tube. Cells remaining in the vial were resuspended with 1.0 mL of pre warmed Complete HT Medium and added to the conical tube. The tube was capped and then gently inverted several times to resuspend the hepatocytes. The cell suspension was centrifuged at 50× g at room temperature for 5 minutes and the supernatant discarded. The cell pellet was loosened by gently swirling the centrifuge tube and Supplemented KHB medium was added to obtain a target density of 2×10⁶ cells/mL. The total cell count and the proportion of viable cells were determined by Trypan Blue dye exclusion using a hemocytometer.

For incubations, aliquots of hepatocyte suspension (250 μl containing 500,000 cells) were added to 250 μl of 2 μM test compound or metabolic stability controls in supplemented KHB in duplicate wells in a 24-well plate. Final concentration in the incubations were 1×10$^6$ cells/mL and 1 μM test compound. 7-Hydroxycoumarin and testosterone, compounds known to be efficiently metabolized by hepatocytes, were used as positive controls in parallel incubations (2 μM final concentration of each compound). The incubation was carried out with gentle shaking at 37° C. under a humid atmosphere of 95% air/5% $CO_2$ (v/v). Aliquots (50 μL) were removed after 0, 1, 3, and 6 hours and added to 100 μl IS/Q quenching solution. After termination, 150 μl of water was added, the plates were centrifuged at 3000×g for 10 min, and aliquots of the supernatant were analyzed on a Micromass Quattro Premier mass spectrometer coupled to an Agilent 1200 Series HPLC system with a Leap Technologies HTC PAL autosampler as described below.

Liquid Chromatography—Mass Spectrometry:

Quantification of test compound and metabolic stability controls was performed by analyte/internal standard peak area ratios (PAR) measured on a Micromass Quattro Premier XL tandem triple quadrupole mass spectrometer coupled to an Agilent 1200 Series HPLC system with a Leap Technologies HTC PAL autosampler. The column used was a Phenomenex® MercuryMS™, Synergi Max-RP (100 Å pore size, 2.5 μm particle size, 20×2.0 mm). Mobile Phase A consisted of 0.2% (v/v) formic acid in 99% water/1% acetonitrile (v/v). Mobile Phase B consisted of 0.2% (v/v) formic acid in 5% water/95% acetonitrile (v/v). Elution was achieved by the following series of linear gradients: initial conditions of 0% B, holding for 30 s, then increasing to 100% B over 90 s, and then returning to the initial conditions over 1 s. The system was allowed to re-equilibrate for a minimum of 60 s between injections. The sample injection volume was 10 μL.

LTP Plasma Protein Binding:

A stock solution of test compound in dimethyl sulfoxide (DMSO) having a final concentration of 10 mM was prepared and used in all experiments.

Commercially available chemicals were obtained from Sigma-Aldrich (St. Louis, Mo.) and VWR (West Chester, Pa.). The cell culture medium (CCM) was Gibco Dulbecco's Modified Eagle Medium (DMEM) with 10% (v/v) fetal bovine serum.

Equilibrium Dialysis Assay:

Pooled plasma (from at least 3 males and 3 females) was from human, beagle dog, Sprague-Dawley rat, cynomolgus monkey, and rhesus monkey. Sodium EDTA was used as the anticoagulant.

Competitive equilibrium dialysis was conducted at 37° C. using human plasma versus with CCM containing 10% of FBS, both sides of matrix spiked with sample at final concentrations of 2 μM. Prior to the study, dialysis membrane was soaked for approximately one hour in 0.133 M phosphate buffer, pH 7.4. Spiked plasma (1 mL) and CCM (1 mL) were placed into opposite sides of the assembled dialysis cells. For assessment of recovery, after the 24-hour equilibration period in a 37° C. water bath, plasma samples were drained into pre-weighed polypropylene tubes containing 1 mL of CCM (without compound) and CCM samples were drained into pre-weighed tubes containing 1 mL of related blank plasma. Post-dialysis plasma and CCM weights were measured and recorded for calculations.

Liquid Chromatography—Mass Spectrometry:

The quantification of test compound was performed by analyte/internal standard peak area ratios (PAR) measured on a Q-Exactive mass spectrometer coupled to an Agilent 1260 Series HPLC system with a Leap Technologies HTS PAL autosampler. Mobile Phase A consisted of 0.2% (v/v) formic acid in 99% water/1% acetonitrile (v/v). Mobile Phase B consisted of 0.2% (v/v) formic acid in 5% water/95% acetonitrile (v/v). The sample injection volume was 10 μL.

$pK_a$ Determinations:

Sample Preparation: A stock solution of test compound in dimethyl sulfoxide (DMSO) having a final concentration of 10 mM was prepared and used in all experiments. The DMSO stocks were thawed, spun, and sonicated in a 40° C. water bath to facilitate dissolution.

$pK_a$ Analysis: The 10 mM DMSO stock solutions were diluted 100 fold with 10 mM HCl for a final compound concentration of 100 μM and 1% DMSO. The compounds were then transferred into 24 consecutive wells of a 96 well PCR plate for analysis with the aqueous method. For compounds that did not give high quality data in the aqueous method, the 10 mM DMSO stock solutions were diluted 100 fold with 2 mM HCl and methanol, such that the final concentration of methanol was 60%, compound concentration was 100 μm, and DMSO concentration was 1%. The compounds were transferred into 24 consecutive wells of a 96 well plate for analysis using the co-solvent method.

Analysis: All data was obtained using a pKa PRO Analyzer (AATI, Ames, Iowa). For the aqueous method, an electrophoretic separation is performed in parallel across 24 different pH values, providing a direct measure of overall compound charge vs. pH. The compounds are detected by UV at 228 nm. The average pH spacing between buffer points is 0.4 pH units covering a typical pH range of 1.7-11.2.

The co-solvent method is suitable for analysis of compounds possessing low aqueous solubility (typically a predicted intrinsic solubility of <10 μg/ml). The average pH spacing between buffer points is 0.4 pH units covering a pH range of 1.7-11.2. Four consecutive CE runs are performed for each compound starting with 60% co-solvent buffers and decreasing to 30% co-solvent buffers.

Norfloxacin is used as a daily performance-indicating standard.

Calculation of Results: The total number of pKa values is predicted by relating mobility and compound molecular weight using pKa Estimator® software (AATI, Ames, Iowa).

Automated hERG Assay at Charles River—Cleveland (Formerly ChanTest)

The FASTPatch® Assay (Charles River,) was used to examine the in vitro effects of various compounds on the cloned hERG potassium channel encoded by the KCNH2 gene and stably expressed in HEK293T cells. Vehicle, test and control article formulations were prepared by diluting DMSO stock solutions in HB-PS (HEPES-buffered physiological saline solution), and were delivered to cells via the QPatch robot pipetting system to a final concentration of 0.3% DMSO. Test compound final concentrations of 0.3, 1, 3, 10 and 30 uM were applied to cells (n 3, where n=the number of cells/concentration) in ascending order in at least three minute intervals separated by solution exchange. The positive control, 50 nM Cisparide, was applied in the same manner. Cell membrane currents were recorded at room temperature with up to 48 parallel patch clamp amplifiers in the QPatch HT® or QPatch HTX® system, and only cells with validated whole-cell recordings (seal resistance ≥200 MΩ and leak current ≤25% channel current) were used. Onset and block of hERG current was measured using a stimulus voltage pattern consisting of a 500 ms prepulse to −40 mV, a 2-second activating pulse to +40 mV, followed by a 2-second test pulse to −40 mV. The pulse pattern was repeated continuously at 10-second intervals from a holding potential of −80 mV. TurboSol analysis for test compound solubility was performed for each concentration tested using a Nephelostar reader measuring light scatter from a 635 nm laser source. Based on validation experiments, light scatter above four times the background level was considered an indication of the presence of particles in suspension.

Results from In Vitro Assays are presented in Table 3, below:

TABLE 3

| compound | $IC_{50}$ HTRF (nM) | $EC_{50}$ TNF (nM) | Protein Adj. $EC_{50}$ TNF (nM) | Human Hep. Stability (L/h/kg) | $pK_a$ | hERG $IC_{50}$ (uM) |
|---|---|---|---|---|---|---|
| A | <1 | 23 | 504 | 0.20 | 6.1 | 3.9 |
| 1 | 2 | 50 | 383 | 0.05 | 6.6 | 1.7 |
| 2 | <1 | 19 | 232 | 0.13 | 5.1 | >10 |
| 3 | <1 | 14 | 191 | 0.08 | 4.9 | >30 |
| 4 | 2 | 115 | | | | |
| 5 | 1 | 60 | | | | |
| 6 | 5 | 267 | | | | |
| 7 | | 164 | | | | |
| 8 | <1 | 33 | | 0.14 | 5.9 | 3.5 |
| 9 | <1 | 49 | | 0.26 | 4.8 | |
| 10 | <1 | 35 | | 0.22 | | |

What is claimed is:

1. A compound of Formula (II):

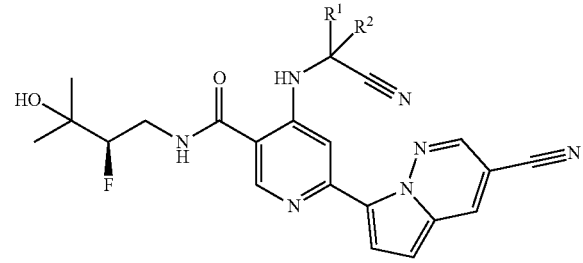

(II)

or a pharmaceutically acceptable salt or structural isomer thereof, wherein:
$R^1$ is H, D or methyl, $R^2$ is H, D or methyl, or $R^1$ and $R^2$, together with the carbon atoms to which they are attached, form cyclopropyl.

2. The compound of claim 1, wherein $R^1$ is H.
3. The compound of claim 1, wherein $R^1$ is methyl.
4. A compound of Formula III:

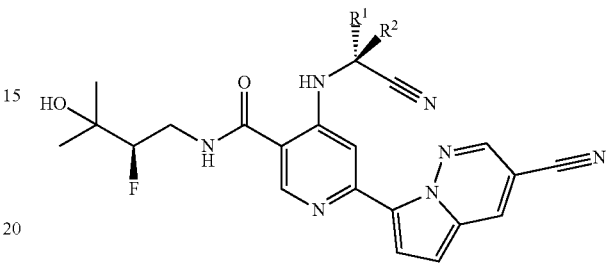

(III)

or a pharmaceutically acceptable salt, deuterated analog thereof, wherein:
$R^1$ is H, D or methyl; and
$R^2$ is H, D or methyl.

5. The compound

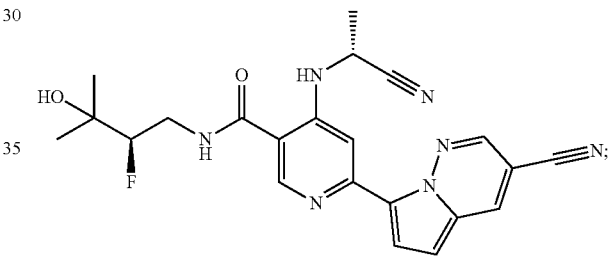

or a pharmaceutically acceptable salt thereof.

6. A pharmaceutical composition comprising a compound of any of claims 1-5, or a pharmaceutically acceptable salt thereof, together with a pharmaceutically acceptable carrier.

* * * * *